United States Patent
Liu et al.

(10) Patent No.: US 9,440,891 B2
(45) Date of Patent: Sep. 13, 2016

(54) PALLADIUM-CATALYZED DECARBONYLATION OF FATTY ACID ANHYDRIDES FOR THE PRODUCTION OF LINEAR ALPHA OLEFINS

(71) Applicant: CALIFORNIA INSTITUTE OF TECHNOLOGY, Pasadena, CA (US)

(72) Inventors: Yiyang Liu, Pasadena, CA (US); Brian M. Stoltz, San Marino, CA (US); Robert H. Grubbs, South Pasadena, CA (US); Alexey Fedorov, Zurich (CH); Kelly E. Kim, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 214 days.

(21) Appl. No.: 14/091,466

(22) Filed: Nov. 27, 2013

(65) Prior Publication Data

US 2014/0155666 A1 Jun. 5, 2014

Related U.S. Application Data

(60) Provisional application No. 61/733,772, filed on Dec. 5, 2012, provisional application No. 61/864,287, filed on Aug. 9, 2013.

(51) Int. Cl.
*C07C 1/24* (2006.01)
*C07C 1/207* (2006.01)

(52) U.S. Cl.
CPC .............. *C07C 1/24* (2013.01); *C07C 1/2078* (2013.01); *C07C 2531/24* (2013.01); *C07C 2531/30* (2013.01)

(58) Field of Classification Search
CPC ............................ C07C 1/24; C07C 1/2078
USPC ................... 585/514, 527, 638, 654
See application file for complete search history.

(56) References Cited

U.S. PATENT DOCUMENTS 3,530,198 A 9/1970 Fenton et al.

OTHER PUBLICATIONS

Miranda, M.O.; Pietrangelo, A.; Hillmyer, M.A.; Tolman, W.B. "Catalytic decarbonylation of biomass-derived carboxylic acids as efficient route to commodity monomers", Green Chem. (Jan. 5, 2012), 14, pp. 490-494.*
Miller, J.A.; Nelson, J.A.; Byrne, M.P. "A Highly Catalytic and Selective Conversion of Carboxylic Acids to 1-Alkenes of One Less Carbon Atom", J. Org. Chem. (1993), 58, pp. 18-20.*

Gooβen, L., and Rodriquez, N., "A Mild and Efficient Protocol for the Conversion of Carboxylic Acids to Olefins by a Catalytic Decarbonylative Elimination Reaction", Chem. Commun., Mar. 21, 2004, 724-725, Epublished Feb. 18, 2004.
Hollak et al, "Selective Deoxygenation of StearicAcid Via an Anhydride Pathway", RSC Advances, Aug. 14, 2012, 2, 9387-9391.
International Patent Application No. PCT/US2013/072133: International Search Report and the Written Opinion dated Mar. 24, 2014, 10 pages.
Kranenburg et al, "New Diphosphine Ligands Based on Heterocyclic Aromatics Inducing Very High Regioselectivity in Rhodium-Catalyzed Hydroformylation: Effect of the Bite Angle", Organometallics, Jun. 1995, 14(6), 3081-3089.
Kraus, G. and Riley, S., "A Large-Scale Synthesis of α-Olefins and α, ω-Dienes", Synthesis, 2012, 44(19), 3003-3005.
Le Nôtre et al, "Biobased Synthesis of Acrylonitrile From Glutamic Acid", Green Chem., 2011, 13, 807-809, e-pubished Feb. 14, 2011.
Le Nôtre et al, "Selective Preparation of Terminal Alkenes from Aliphatic Carboxylic Acids by a Palladium-Catalysed Decarbonylation—Elimination Reaction", Tetrahedron Letters, Jul. 21, 2010, 51(29), 3712-3715.
Maetani et al, "Efficient Iridium-Catalyzed Decarbonylation Reaction of Aliphatic Carbocylic Acids Leading to Internal or Terminal Alkenes", Organometallics, 2011, 30(6), 1389-1394, e-published Feb. 22, 2011.
Maetani et al, "Iron-Catalyzed Decarbonylation Reaction of Aliphatic Carbocylic Acids Leading to a-olefins", Chem. Comm., Jan. 10, 2012, 48, 2552-2554.
Miller et al, "A Highly Catalytic and Selective Conversion of Carboxylic Acids to 1-Alkenes of One Less Carbon Atom", J. Org. Chem., Jan. 1993, 58(1), 18-20.
Miranda et al, "Catalytic Decarbonylation of Biomass-Derived Carboxylic Acids as Efficient Route to Commodity Monomers", Green Chemistry, Jan. 5, 2012, 14, 490-494.
Sen, A., and Lai, T., "Mechanism of Palladium( 11)-Catalyzed C=C Bond Isomerization in Olefins", Inorg. Chem., Sep. 1984, 23(20), 3257-3258.
Van Leeuwen et al, "The Bite Angle Makes the Catalyst", Pure Appl. Chem., 1999, 71(8), 1443-1452.

* cited by examiner

*Primary Examiner* — In Suk Bullock
*Assistant Examiner* — Aaron Pierpont
(74) *Attorney, Agent, or Firm* — Baker & Hostetler LLP

(57) ABSTRACT

The present invention is directed to methods of forming olefins, especially linear alpha olefins from fatty acids or anhydrides, each method comprising: contacting an amount of precursor carboxylic acid anhydride with a palladium catalyst comprising a bidentate bis-phosphine ligand in a reaction mixture so as to form an olefin in a product with the concomittant formation and removal of CO and water from the reaction mixture, either directly or indirectly, wherein the reaction mixture is maintained with a sub-stoichiometric excess of a sacrificial carboxylic acid anhydride, an organic acid, or both, said sub-stoichiometric excess being relative to the amount of the precursor carboxylic acid anhydride. The precursor carboxylic acid anhydride may be added to the reaction mixture directly or formed in situ by the reaction between at least one precursor carboxylic acid with a stoichiometric amount of the sacrificial acid anhydride.

25 Claims, No Drawings

PALLADIUM-CATALYZED DECARBONYLATION OF FATTY ACID ANHYDRIDES FOR THE PRODUCTION OF LINEAR ALPHA OLEFINS

CROSS REFERENCE TO RELATED APPLICATIONS

This application claims priority to U.S. Patent Application Ser. Nos. 61/733,772, filed Dec. 5, 2012, and 61/864,287, filed Aug. 9, 2013, the contents of each application are incorporated by reference herein for all purposes.

GOVERNMENT RIGHTS

This invention was made with government support under Grant No. GM080269 and under Grant No. GM031332 awarded by the National Institutes of Health. The government has certain rights in the invention.

TECHNICAL FIELD

The present invention relates to catalysis, especially catalytic methods of forming linear alpha olefins.

BACKGROUND

Linear Alpha Olefins represent an important class of industrial chemicals with a wide range of applications. They are used as co-monomers for ethylene polymerization as well as precursors to plasticizers, lubricants, and surfactants. Currently, these olefins are mainly produced by oligomerization of ethylene, which, in turn, is derived from petroleum. As the world's oil reserves continue to diminish, development of renewable feedstocks for the production of alpha olefins becomes increasingly important. One obvious choice is ethylene from biomass-derived ethanol. A more direct method is the decarbonylative dehydration of long chain fatty acids. The latter route is particularly attractive because fatty acids are inexpensive and readily available starting materials derived from many natural sources. Since natural fatty acids contain an even number of carbon atoms, their corresponding alpha olefins will be odd-numbered after decarbonylative dehydration. Moreover, conventional ethylene oligomerization processes deliver only even-numbered alpha olefins, and odd-numbered olefins are largely inaccessible. These odd-numbered olefins are valuable building blocks in the synthesis of various fine chemicals such as lepidopteran insect pheromones, but are currently far too costly to be practical. Therefore, the development of an efficient and economic process for fatty acid decarbonylation is highly desirable.

Many strategies to convert fatty acids to alpha olefins have been pursued. Lead tetraacetate-mediated oxidative decarboxylation is a classical method. Alternative protocols that avoid stoichiometric toxic reagents have also been developed, such as Kolbe electrolysis and silver-catalyzed oxidative decarboxylation. However, these reactions proceed through highly reactive radical intermediates, and thus suffer from low yields due to many side reactions. A more recent approach entails the transition metal-catalyzed decarbonylative dehydration of fatty acids. A variety of transition metals including rhodium, iridium, palladium, and iron have been shown to catalyze decarbonylative dehydration reactions. To date, palladium has demonstrated the highest activity, and catalyst loadings as low as 0.01 mol % have been reported independently by Miller and Kraus. Unfortunately, their methods require very high temperatures (230-250° C.). In addition, it is necessary to distill the olefin product from the reaction mixture as soon as it is formed in order to prevent double bond isomerization, and therefore only volatile olefins can be produced this way. Decarbonylation processes under milder conditions have been developed independently by Gooβen and Scott. Although their reactions proceed at 110° C., much higher palladium catalyst loading (3 mol %) and an expensive, high-boiling-point solvent (DMPU, 1,3-dimethyl-3,4,5,6-tetrahydro-2(1H)-pyrimidinone) are required.

The present invention addresses at least some of these deficiencies in the art.

SUMMARY

Various embodiments of the present invention provide methods of forming olefins, especially terminal (alpha) olefins from fatty acids or fatty acid anhydrides, each method comprising: contacting an amount of precursor carboxylic acid anhydride with a palladium catalyst comprising a bidentate bis-phosphine ligand in a reaction mixture so as to form an olefin in a product with the concomitant formation and removal of CO and water from the reaction mixture, either directly or indirectly, wherein the reaction mixture is maintained with a sub-stoichiometric excess of a sacrificial carboxylic acid anhydride, an organic acid, or both, said sub-stoichiometric excess being relative to the amount of the precursor carboxylic acid anhydride. The precursor carboxylic acid anhydride may be added to the reaction mixture directly or formed in situ by the reaction between at least one precursor carboxylic acid with a stoichiometric amount of the sacrificial acid anhydride.

DETAILED DESCRIPTION OF ILLUSTRATIVE EMBODIMENTS

The present invention is directed to methods of forming olefins, especially terminal (alpha) olefins from fatty acid precursors, based on contacting precursor carboxylic acid anhydrides with certain palladium catalysts comprising a bidentate bis-phosphine ligand in a reaction mixture so as to form an olefin in a product with the concomitant formation and removal of CO and water from the reaction mixture, either directly or indirectly. In preferred embodiments, the reaction mixture is maintained with a sub-stoichiometric excess of a sacrificial carboxylic acid anhydride, an organic acid, or both, said sub-stoichiometric excess being relative to the amount of the precursor carboxylic acid anhydride. The precursor carboxylic acid anhydride may be added to the reaction mixture directly or formed in situ by the reaction between at least one precursor carboxylic acid with a stoichiometric amount of the sacrificial acid anhydride. The remarkable facility and regiospecificity exhibited by at least some of these systems provides a useful tool kit for chemists in these fields.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) is the facile operability of the methods (or the systems used in such methods or the compositions derived therefrom) to selectively decarbonylatively dehydrate carboxylic acids or anhydrides, including fatty acids or fatty acid anhydrides, to form alpha olefins.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Various embodiments of the present invention provide methods of forming olefins, especially useful for the formation of linear alpha olefins, by decarbonylative dehydration of carboxylic acids or anhydrides, including fatty acids or fatty acid anhydrides, each method comprising: contacting an amount of a precursor carboxylic acid anhydride with a palladium catalyst comprising a bidentate bis-phosphine ligand in a reaction mixture so as to form an olefin in a product with the concomitant formation and removal of CO and water from the reaction mixture, either directly or indirectly, wherein the reaction mixture is maintained with a sub-stoichiometric excess of a sacrificial carboxylic acid anhydride, an organic acid, or both, said sub-stoichiometric excess being relative to the amount of the precursor carboxylic acid anhydride. In other embodiments, the methods include those where the reaction mixture consists essentially of (a) the precursor carboxylic acid anhydride, (b) a palladium catalyst comprising a bidentate bis-phosphine ligand, and (c) the sacrificial acid anhydride, the organic acid, or both the sacrificial acid anhydride and the organic acid.

The reactions can be done neat or in the presence of a non-reactive solvent, though preferably the reactions are conducted in the absence of solvent (i.e., neat). That is, in various embodiments, the reactions are conducted in the absence of extraneous solvent, and especially in the absence of DMPU (1,3-dimethyl-3,4,5,6-tetrahydro-2(1H)-pyrimidinone). The reactions are best done under inert atmosphere. The reactions can be done at temperatures in range of from about 80° C. to about 200° C., preferably from about 100° C. to about 160° C. The temperatures used in the Examples also represent independent embodiments. Under such conditions, any water liberated by the process from the precursors generally reacts with one of the sacrificial anhydrides in the reaction mixture and is removed as the lowest boiling carboxylic acid. In certain embodiments, the reaction may be conducted under reduced pressure (including, for example, in a range of from about 1 mm Hg to about 25 mm Hg) or at alternating intervals of ambient pressure (ca. 1 atm) and reduced pressure, the reduced pressure allowing for the more efficient removal of the reaction by-products, the product olefins themselves, or both the by-products and products.

As described above, palladium catalyzed decarbonylative dehydrations are known in the art, but these prior systems either require high temperatures, are prone to double bond migration in the final product, or require the specific use of an expensive, high-boiling-point solvent (DMPU, 1,3-dimethyl-3,4,5,6-tetrahydro-2(1H)-pyrimidinone). Proposed catalytic cycles for general transition metal systems can be described in terms of oxidative addition of an anhydride precursor to the metal center to form an acyl carboxylate, decarbonylation of the acyl moiety, followed by reductive elimination of a carboxylic acid and olefin, and decarbonylation of the reduced metal center.

By contrast, the systems of the present invention can be operated at modest temperatures without the use of any solvent, and yield linear alpha olefins in high yields and selectivities. Several features appear to be important in this enhanced activity and selectivity—including the particular catalyst ligand system, and the presence of excess sacrificial anhydride, and organic acid, or both.

In some embodiments, the precursor carboxylic acid anhydride may be added to the reaction mixture directly as such or formed in situ by the reaction between at least one precursor carboxylic acid with a stoichiometric amount of the sacrificial acid anhydride.

As shown in the Examples, good yield and selectivity is obtained if an organic acid that is structurally resistant to decarbonylative dehydration is added to the reaction mixture. Very good results have been achieved, for examples by adding wherein the organic acid comprises a substituted benzoic acid, substituted hydroxybenzamide, substituted phenol, or a substituted bisphenol, with more specific embodiments shown in the Examples. (see, e.g., Examples 2.5, 2.6, and 3.1). (t-Bu)$_4$biphenol, with or without the use of the sacrificial acid anhydrides appears to be particularly attractive in this regard. The mechanism for this improvement is not understood, but in some cases may involve formation of intermediate anhydrides that are kinetically preferred as substrates to the catalyst.

In other embodiments, good results can be achieved by the incremental addition of so-called sacrificial acid anhydrides during the course of the decarbonylative dehydration reactions. These sacrificial acid anhydrides are preferably formed of carboxylic acids whose boiling points are less than the boiling points of the carboxylic acids of the precursor anhydrides. In preferred embodiments this sub-stoichiometric excess of the sacrificial acid anhydride is present in an amount sufficient to favor the presence of the precursor carboxylic acid anhydride with respect to its corresponding precursor carboxylic acid or acids, in part because the sacrificial acid anhydride is converted to its corresponding lower boiling carboxylic acid, which is then preferentially removed from the reaction mixture by vacuum distillation or other fractionation method. It is also preferred, but not necessary, that the sacrificial carboxylic acid anhydride is structurally resistant to decarbonylative dehydration, so as not to tie up the catalyst in non-productive cycles. Particularly preferred sacrificial acid anhydrides include those comprising volatile carboxylic acids, for example acetic anhydride, benzoic anhydride, isobutyric anhydride, propionic anhydride, or pivalic anhydride.

Depending on the reactivity of the specific precursor anhydrides, the sub-stoichiometric excess of the sacrificial acid anhydride should be present in an amount ranging from about 0.01 to about 0.9, relative to the original amount of the precursor carboxylic acid anhydride. In other embodiments, this stoichiometric excess is present in a range having a lower boundary of about 0.01, about 0.025, about 0.05, or 0.1 and an upper boundary of about 0.9, about 0.8, about 0.7, about 0.6, about 0.55, or about 0.55, with one exemplary range being from about 0.01 to about 0.55. In order to maintain these excesses, the sacrificial acid anhydride may be added incrementally during the course of the reaction at time intervals between successive incremental additions in a range of from about 5 min, about 10 min, or about 15 min to about 30 min, about 60 min, or about 90 minutes. More specific embodiments with respect to these time intervals are also described in the Examples.

The precursor acid anhydrides are not limited in structure, so long as one of the acids of the anhydride is capable of undergoing decarbonylative dehydration (see, for example, the types of structures shown in Table 14 for certain non-limiting examples). In certain embodiments, the precursor carboxylic acid anhydride is an acid anhydride of at least one fatty acid. That is, the acid anhydride may be formed of two of the same or different fatty acids or a fatty acid and a non-fatty acid carboxylic acid or a combination thereof. As used herein, the term "fatty acid" refers to a carboxylic acid with a long aliphatic tail (chain), which is either saturated or unsaturated. Fatty acids encompass both naturally occurring fatty acid chains (having an even number of carbon atoms, from 4 to 28, typically derived from triglycerides or phospholipids) or synthetic fatty acids (having an odd number of carbon atoms, from 3 to 27, typically derived from petroleum sources. The fatty acids or fatty acid anhydrides may be saturated or singly or multiply unsaturated. Where unsaturated, the double bonds may be cis or trans, and it appears, at least on some embodiments, that the inventive methods does not alter the cis/trans-character or position of the internal double bonds. Exemplary naturally occurring unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. Exemplary naturally occurring saturated fatty acids include caprylic acid, capric acid, lauric acid, myristic acid, palmitic acid, stearic acid, arachidic acid, behenic acid, lignoceric acid, and cerotic acid.

Additionally, alternatively, or both, the precursor carboxylic acid anhydride can be an acid anhydride having at least one moiety functionalized by any of the functional groups described above as "Fn", and preferably by an alkoxycarbonyl, ester, halide, imide, ketone, protected amine, terminal or alpha olefin, or substituted aromatic, such that the product has an alpha olefin at one end and the described functional group at the other end of the product. Examples of such functionalized precursors are shown in Example 3.1, Table 14.

The method provides for facile syntheses of linear alpha olefins from fatty acid precursors, and generally alpha olefins wherein the precursor comprises a primary carboxylic acid or anhydride moiety. Where the precursor comprises a secondary carboxylic acid or anhydride moiety, the reaction proceeds to form internal olefins (see, e.g., Table 14). As used herein, unless otherwise stated, a product having an "alpha olefin" refers to a product in which at least 80% of the olefin formed by the inventive method is an alpha olefin, relative to the total olefin formed by the method. However, other embodiments provide that the product having an "alpha olefin" at one end may describe a product having at least about 80%, about 90%, about 95%, or at least about 98% of alpha olefin, relative to the total olefin formed by the inventive method.

Certain aspects of the present invention include those embodiments where the palladium catalyst is present in a range of from about 0.0001 mole percent to about 0.5 mole percent, relative to the amount of the precursor carboxylic acid or anhydride originally present in the reaction mixture. Other independent embodiments include those where the palladium is present in a range of from about 0.0001 to about 0.001 mole percent, or from about 0.001 to about 0.01 mole percent, or from about 0.01 to about 0.05 mole percent, from about 0.05 to about 0.1 mole percent, or from about 0.1 mole percent to about 0.2, to about 0.3, to about 0.4, to about 0.5, or to about 1 mole percent, relative to the amount of the precursor carboxylic acid or anhydride originally present in the reaction mixture. Higher catalyst loadings may also be used, but do not appear to be necessary for high yields or selectivities.

The invention is described in terms of a palladium catalyst comprising a bidentate bis-phosphine ligand. Good yields and selectivities have been realized with bidentate phosphine ligand to palladium ratios as high as 4:1, in preferred embodiments, the ratio of the bidentate phosphine ligand to palladium in the palladium bidentate bis-phosphine catalyst is in a range of from about 0.9:1 to about 1.5:1, preferably from about 1:1 to about 1.2:1. The palladium catalyst comprising the bidentate bis-phosphine ligand is generated in situ from non-phosphine or mono-phosphine palladium precursors, in which case it appears preferable to provide for a slight excess of ligand to ensure fully formed. In such cases, the ratio of the bidentate phosphine ligand to palladium is preferably in a range of from about 1.1:1 to about 4:1, from about 1.1:1 to about 2:1, from about 1.1:1 to about 1.5:1, and more preferably about 1.2:1. See, e.g., Tables 11-14

The bite angle of the bidentate bis-phosphine ligand also appears to be an important factor in the reactivity and selectivity of the system, and in certain embodiments, the bite angle in a range of from about 100 degrees to about 130 degrees, preferably including a range of from about 105 to about 120 degrees. See, e.g., Example 2.1, Table 1. The term "bite angle" is recognized in the field of transition metal phosphine chemistry and refers to the P-M-P angle of the transition metal, M, complex, as dictated by the steric features of the bidentate P~P ligand.

In preferred embodiments, the bidentate bis-phosphine ligand comprises a structure of Formulae (I) or (II):

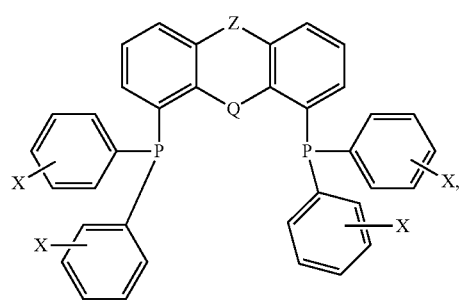

(I)

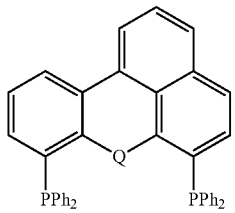

(II)

wherein
  Q is O;
  Z is —O—; —S—; —CH₂— or —C(R)₂—; —C(=CR₂)—) —P(aryl)-; —P(heteroaryl)-; —Si(R)₂—; or —N(R)—; provided at least one of Q or Z are not absent (i.e., when Q is absent, Z is not absent; when Z is absent, Q is not absent; or both Q and Z are not absent;
  each R is independently at each occurrence H, lower chain alkyl (e.g., methyl), aryl (e.g., phenyl), or aralkyl (e.g., benzyl); and
  X is independently at each occurrence H, F, Cl, C$_{1-3}$ alkyl, or C$_{1-3}$ alkoxide.

In some preferred embodiments, X is H. In some embodiments, X is independently at each occurrence F, Cl, methyl, or methoxy substituted in the 2 or 4 position.

In some embodiments, the bidentate bis-phosphine ligand comprises a structure of Formulae (IA)

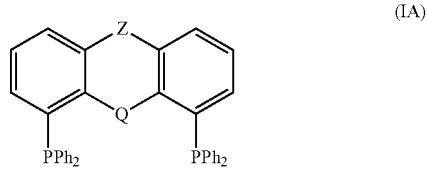

(IA)

wherein Q and Z are as defined above.

In some embodiments, the bidentate bis-phosphine ligand comprises a ligand of:

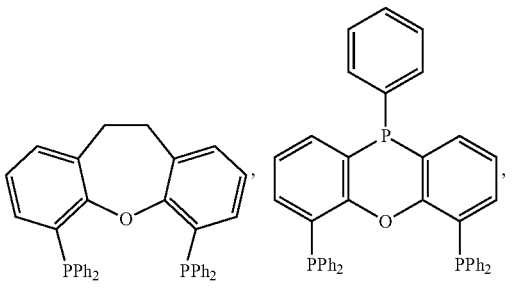

,

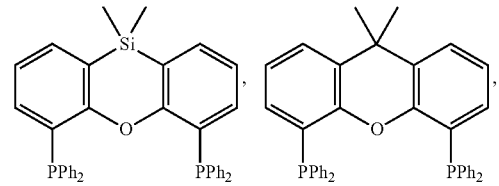

,

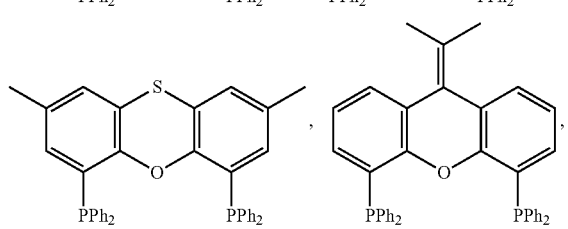

,

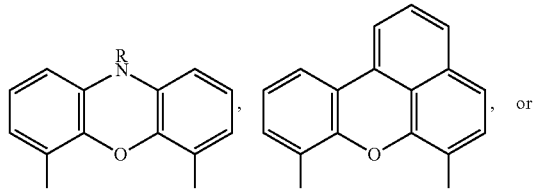

, or

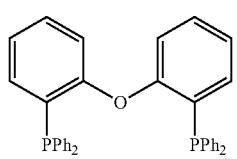

In more preferred embodiments, the bidentate bis-phosphine ligand comprises a Xantphos ligand or a DPEphos ligand:

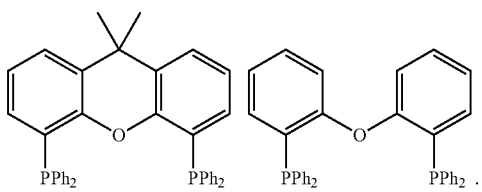

The reaction mixture may also further comprise an optionally substituted monodentate triarylphosphine or monodentate tri-heteroarylphosphine ligand. Such ligands may be added separately or accompany a palladium catalyst precursor. In certain preferred embodiments, this optionally monodentate triarylphosphine or monodentate tri-heteroarylphosphine ligand may comprise an optionally substituted triphenylphosphine or tripyridylphosphine ligand, particularly one containing electron withdrawing substituents. Such monophosphines, in some cases, offer compromised reactivity and improved selectivity. Some exemplary triphenylphosphine ligands are illustrated in Examples 2.1 and 2.3.

While not intending to be bound by the correctness of any particular theory, it appears that the presence of the monophosphines act to suppress the isomerization of the first formed alpha olefins. In this context, it is also observed that tertiary amines also act to suppress isomerization. This feature of amines is especially important when the acid from the sacrificial anhydride would otherwise tend to accumulate in the system. See, e.g., Examples 2.7 and 2.8.

Terms

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or oligomeric or polymeric analogs thereof.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing such "aromatic moieties." The term "aromatic moieties" is intended to refer to those portions of the compounds, oligomers, or polymers having an indicated aromatic structures. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2OH$), sulfonate($SO_2O$—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H) alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (—$B(OH)_2$), boronato (—$B(OR)_2$ where R is alkyl or other hydrocarbyl), phosphono (—$P(O)(OH)_2$), phosphonato (—$P(O)(O)_2$), phosphinato ($P(O)(O$—)), phospho (—$PO_2$), and phosphine (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl] MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The following listing of embodiments is intended to complement, rather than displace or supersede, the previous descriptions.

Embodiment 1. A method for forming olefins, said method comprising: contacting an amount of precursor carboxylic acid anhydride with a palladium catalyst comprising a bidentate bis-phosphine ligand in a reaction mixture so as to form an olefin in a product with the concomitant formation and removal of CO and water from the reaction mixture, wherein the reaction mixture is maintained with a sub-stoichiometric excess of a sacrificial carboxylic acid anhydride, an organic acid, or both, said sub-stoichiometric excess being relative to the amount of the precursor carboxylic acid anhydride.

Embodiment 2. The method of Embodiment 1, wherein the precursor carboxylic acid anhydride is formed in situ by the reaction between at least one precursor carboxylic acid with a stoichiometric amount of the sacrificial acid anhydride.

Embodiment 3. The method of Embodiment 1 or 2, wherein the sub-stoichiometric excess of the sacrificial acid anhydride is added incrementally during formation of the olefin.

Embodiment 4. The method of any one of Embodiments 1 to 3, wherein the sub-stoichiometric excess of the sacrificial acid anhydride is present in an amount sufficient to favor the presence of the precursor carboxylic acid anhydride with respect to its corresponding precursor carboxylic acid or acids.

Embodiment 5. The method of any one of Embodiments 1 to 4, wherein the sub-stoichiometric excess of the sacrificial acid anhydride is present in an amount ranging from about 0.01 to about 0.9, relative to the original amount of the precursor carboxylic acid anhydride.

Embodiment 6. The method of any one of claims 1 to 5, wherein the sacrificial acid anhydride is converted to its corresponding carboxylic acid.

Embodiment 7. The method of any one of Embodiments 1 to 6, wherein the sacrificial acid anhydride comprises acetic anhydride, benzoic anhydride, isobutyric anhydride, propionic anhydride, or pivalic anhydride.

Embodiment 8. The method of any one of Embodiments 1 to 7, wherein the organic acid comprises a substituted benzoic acid, substituted hydroxybenzamide, substituted phenol, or a substituted bisphenol.

Embodiment 9. The method of any one of Embodiments 1 to 8, wherein the CO and water is removed from the reaction mixture by distillation.

Embodiment 10. The method of any one of Embodiments 1 to 9, wherein the precursor carboxylic acid anhydride is an acid anhydride of at least one fatty acid.

Embodiment 11. The method of any one of Embodiments 1 to 10, wherein the precursor carboxylic acid anhydride is an acid anhydride of at least one moiety functionalized by an alkoxycarbonyl, ester, halide, imide, ketone, protected amine, terminal olefin, or substituted aromatic.

Embodiment 12. The method of any one of Embodiments 1 to 11, wherein the olefin in the product comprises at least 80% of alpha olefin, relative to the total olefin formed by the method.

Embodiment 13. The method of any one of Embodiments 1 to 12, wherein the bidentate bis-phosphine ligand has a bite angle in a range of from about 100 degrees to about 130 degrees.

Embodiment 14. The method of any one of Embodiments 1 to 13, wherein the palladium is present in a range of from about 0.01 mole percent to about 0.5 mole percent, relative to the amount of the precursor carboxylic acid anhydride present in the reaction mixture.

Embodiment 15. The method of any one of Embodiments 1 to 14, wherein the ratio of bidentate phosphine ligand to palladium in the palladium bidentate bis-phosphine catalyst is in a range of from about 0.9 to about 2.

Embodiment 16. The method of any one of Embodiments 1 to 15, wherein the bidentate bis-phosphine ligand comprises a structure of Formulae (I) or (II):

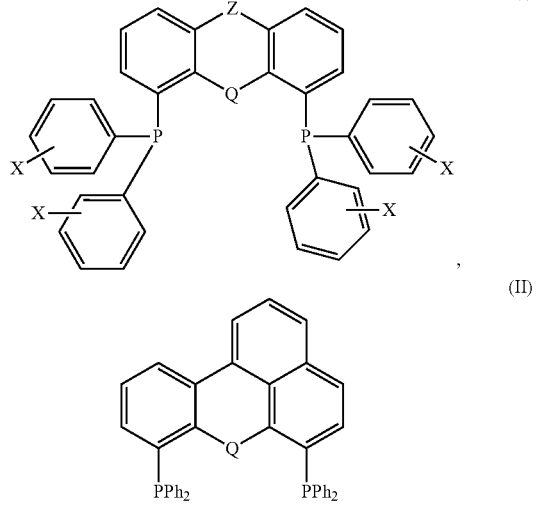

wherein
Q is absent, a bond, or O;
Z is absent; a bond; —O—; —S—; optionally substituted C-2 alkylene (i.e., —CH$_2$— or —C(R)$_2$—); optionally substituted alkenylene (e.g., —C(=CR$_2$)—); —P(aryl)-; —P(heteroaryl)-; —Si(R)$_2$—; or —N(R)—; provided at least one of Q or Z are not absent (i.e., when Q is absent, Z is not absent; when Z is absent, Q is not absent; or both Q and Z are not absent);
each R is independently at each occurrence H, short chain alkyl (e.g., methyl), aryl (e.g., phenyl), or aralkyl (e.g., benzyl); and
X is independently at each occurrence H, F, Cl, C$_{1-3}$alkyl, or C$_{1-3}$alkoxide.

Embodiment 17. The method of any one of Embodiments 1 to 16, wherein the bidentate bis-phosphine ligand comprises a structure of Formulae (IA):

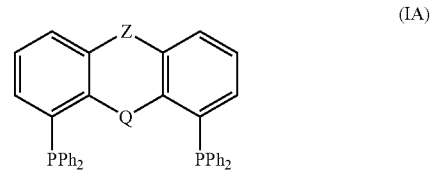

wherein Q and Z are as defined above.

Embodiment 18. The method of Embodiment 16, wherein X is independently at each occurrence F, Cl, methyl, or methoxy substituted in the 2 or 4 position.

Embodiment 19. The method of any one of Embodiments 1 to 17, wherein the bidentate bis-phosphine ligand comprises a Xantphos ligand or a DPEphos ligand:

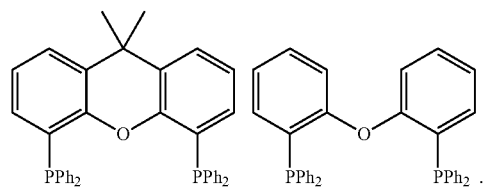

Embodiment 20. The method of any one of Embodiments 1 to 19, wherein the palladium catalyst comprising the bidentate bis-phosphine ligand is generated in situ.

Embodiment 21. The method of any one of Embodiments 1 to 20, wherein the reaction mixture further comprises an optionally substituted monodentate triarylphosphine or monodentate tri-heteroarylphosphine ligand.

Embodiment 22. The method of any one of Embodiments 1 to 21, wherein the reaction mixture further comprises a triphenylphosphine ligand.

Embodiment 23. The method of any one of Embodiments 1 to 22, wherein the reaction mixture consists essentially of (a) the precursor carboxylic acid anhydride, (b) the palladium catalyst comprising a bidentate bis-phosphine ligand, and (c) the sacrificial acid anhydride, the organic acid, or both the sacrificial acid anhydride and the organic acid.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

Materials and Methods

Unless otherwise stated, reactions were performed in flame-dried glassware under a nitrogen atmosphere or under vacuum without the use of solvents. Reaction progress was monitored by $^1$H NMR analysis of the crude reaction mixture. Silicycle SiliaFlash® P60 Academic Silica gel (particle size 40-63 nm) was used for flash chromatography. $^1$H NMR spectra were recorded on a Varian Inova 500 MHz spectrometer and are reported relative to residual CHCl$_3$ (δ 7.26 ppm). $^{13}$C NMR spectra were recorded on a Varian Inova 500 MHz spectrometer (125 MHz) and are reported relative to CHCl$_3$ (δ 77.16 ppm). Data for $^1$H NMR are reported as follows: chemical shift (δ ppm) (multiplicity, coupling constant (Hz), integration). Multiplicities are reported as follows: s=singlet, d=doublet, t=triplet, q=quartet, p=pentet, sept=septuplet, m=multiplet, br s=broad singlet, br d=broad doublet, app=apparent. Data for $^{13}$C NMR are reported in terms of chemical shifts (δ ppm). IR spectra were obtained by use of a Perkin Elmer Spectrum BXII spectrometer using thin films deposited on NaCl plates and reported in frequency of absorption (cm$^{-1}$). High resolution mass spectra (HRMS) were provided by the California Institute of Technology Mass Spectrometry Facility using a JEOL JMS-600H High Resolution Mass Spectrometer by positive-ion FAB, or obtained with an Agilent 6200 Series TOF using Agilent G1978A Multimode source in negative electrospray ionization (ESI−), negative atmospheric pressure chemical ionization (APCI−), or negative mixed ionization mode (NMM: ESI-APCI−).

Reagents were purchased from Sigma-Aldrich, Acros Organics, Strem, or Alfa Aesar and used as received unless otherwise stated.

Example 1.1

Preparation of Lauric Acid Anhydride

A 250-mL round-bottom flask equipped with a magnetic stir bar was charged with lauric acid (100 g, 500 mmol, 1 equiv.) and acetic anhydride (52 mL, 551 mmol, 1.1 equiv). A vacuum-jacketed short path distillation head equipped with a 100-mL round-bottom receiving flask as fitted to the reaction flask. The system was quickly evacuated and back-filled with N$_2$ (3 times), and the reaction flask was gradually heated to 170° C. in an oil bath. Distillation began at about 165° C. and approximately 25 mL colorless liquid was collected. When distillation subsided, the receiving flask was replaced with an empty one, and the system was carefully evacuated such that another portion of liquid (ca. 25 mL) distilled out. The vacuum was continuously increased until no more liquid distilled. The distillation head was removed, and the pale yellow reaction mixture was held under high vacuum (ca. 1 mm Hg) at 180° C. with stirring until $^1$H NMR analysis showed greater than 95% purity of lauric anhydride. The liquid reaction mixture was allowed to cool to room temperature, forming a waxy solid (92 g, 96% yield). $^1$H NMR analysis confirmed the product to be lauric anhydride.

Example 2

Screening Experiments—Effects of Various Parameters

Example 2.1

Phosphine Ligand Screen

Initial screening of phosphine ligands was done according to the following scheme, with the results presented in Table 1:

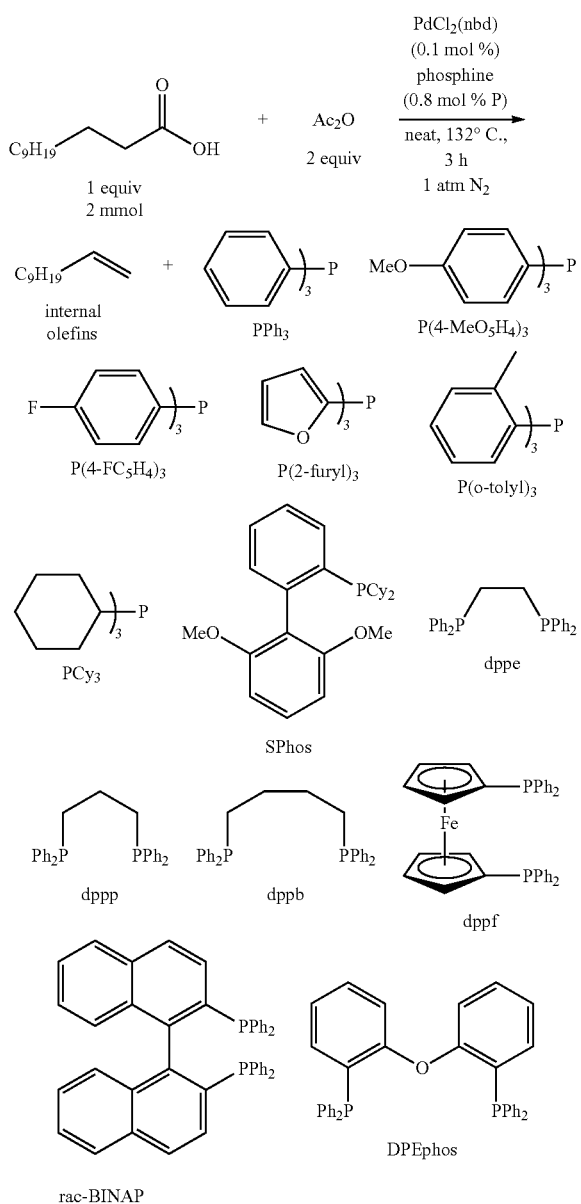

-continued

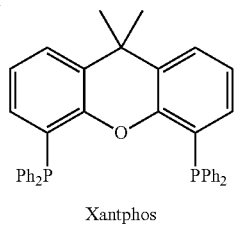

Xantphos

TABLE 1

Phosphine screening experiments

| Entry | Phosphine | Bite Angle, deg | % Yield[a] | % Alpha Olefin[a] |
|---|---|---|---|---|
| 1 | PPh₃ | — | 9 | 85 |
| 2 | P(4-MeOC₆H₄)₃ | — | <5 | |
| 3 | P(4-FC₆H₄)₃ | — | <5 | |
| 4 | P(2-furyl)₃ | — | <5 | |
| 5 | P(o-tolyl)₃ | — | <5 | |
| 6 | PCy₃ | — | 0 | |
| 7 | SPhos | — | 5 | 94 |
| 8 | Dppe | 85 | 0 | |
| 9 | Dppp | 91 | 0 | |
| 10 | Dppb | 98 | 0 | |
| 11 | Dppf | 96 | 0 | |
| 12 | Rac-BINAP | 85 | 0 | |
| 13 | DPEphos | 102 | 29 | 61 |
| 14 | Xantphos | 111 | 58 | 52 |

[a]Determined by gas chromatography with tridecane as internal standard

Example 2.2

Effects of the Ligand-to-Metal Ratio

Experiments were conducted to determine the effect of ligand-to-metal ratios according to the following scheme, with the results presented in Table 2.

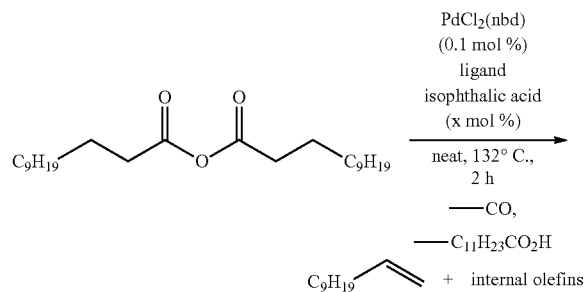

TABLE 2

Effects of the ligand-to-metal ratio

| Entry | Ligand (mol %) | x (mol %) | % Yield[a] | % Alpha[a] |
|---|---|---|---|---|
| 1 | Xantphos (0.4) | 10 | 60 | 75 |
| 2 | Xantphos (0.2) | 10 | 61 | 71 |
| 3 | Xantphos (0.1) | 10 | 82 | 46 |
| 4 | NiXantphos (0.2) | 10 | 79 | 63 |
| 5 | NiXantphos (0.1) | 10 | 90 | 44 |
| 6 | Xantphos (0.2) | 5 | 48 | 80 |
| 7[b] | Xantphos (0.1) | 5 | 74 | 58 |

TABLE 2-continued

Effects of the ligand-to-metal ratio

| Entry | Ligand (mol %) | x (mol %) | % Yield[a] | % Alpha[a] |
|---|---|---|---|---|
| 8 | NiXantphos (0.2) | 5 | 61 | 77 |
| 9 | NiXantphos (0.1) | 5 | 69 | 60 |

[a]Determined by gas chromatography with tridecane as internal standard

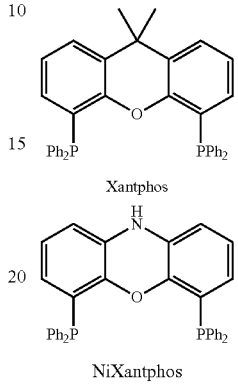

Xantphos

NiXantphos

Example 2.3

Effect of Added Mono-Phosphine

Additional experiments are conducted to determine the effect of added monophosphine according to the following scheme, with the results presented in Table 3:

TABLE 3

Effect of phosphines on yields and selectivity

| Entry | Mono Phosphine (mol %) | % Yield[a] | % Alpha[a] |
|---|---|---|---|
| 1 | None | 80 | 24 |
| 2 | PPh₃ (0.4) | 69 | 50 |
| 3 | PPh₃ (0.8) | 68 | 49 |
| 4 | PPh₃ (1.5) | 52 | 69 |
| 5 | P[3,5-(CF₃)₂C₆H₃]₃ (1.5) | 46 | 76 |
| 6 | P(4-FC₆H₄)₃ (1.5) | 12 | 91 |
| 7 | P(2-furyl)₃ (1.5) | 43 | 80 |
| 8 | P(4-MeOC₆H₄)₃ (1.5) | 58 | 47 |

[a]Determined by gas chromatography with tridecane as internal standard

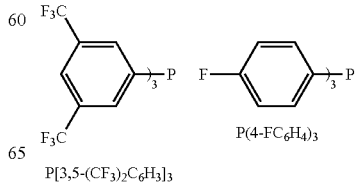

P[3,5-(CF₃)₂C₆H₃]₃          P(4-FC₆H₄)₃

TABLE 3-continued

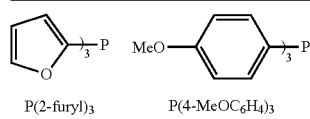

P(2-furyl)$_3$   P(4-MeOC$_6$H$_4$)$_3$

Example 2.4

Sacrificial (Activator) Anhydride Screen

Initial screening of sacrificial (activator) anhydrides was done according to the following scheme, with the results presented in Table 4:

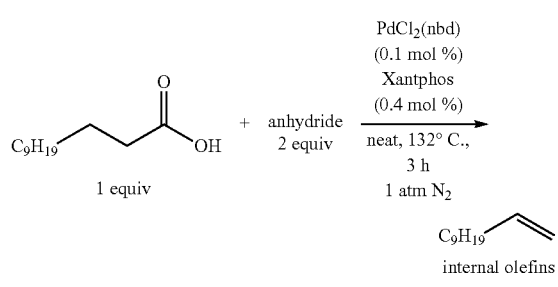

TABLE 4

Initial anhydride screening experiments

| Entry | Sacrificial Anhydride | % Yield$^a$ | % Alpha Olefin$^a$ |
|---|---|---|---|
| 1 | (CH$_3$CO)$_2$O | 58 | 52 |
| 2 | (C$_6$H$_5$CO)$_2$O | 80 | 24 |
| 3 | (ClCH$_2$CO)$_2$O | 0 | — |

$^a$Determined by gas chromatography with tridecane as internal standard

Example 2.5

Acid Additive Screen—Stoichiometric Acids

Initial screening of acid additives was done according to the following scheme and representative procedure, with the results presented in Tables 5 and 6.

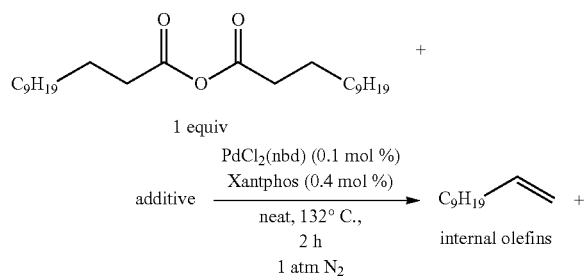

Representative procedure for decarbonylation of lauric anhydride (Table 6, entry 3): A 16 mm×150 mm reaction tube equipped with a magnetic stirbar was charged with a solution of PdCl$_2$(nbd) [nbd=norbornadiene] in CH$_2$Cl$_2$ (1 mL, 0.5 mg/mL). The solvent was evaporated to leave a thin film of yellow solid at the bottom of the reaction tube. Lauric anhydride (765 mg, 2.0 mmol, 1 equiv), Xantphos (4.6 mg, 0.008 mmol, 0.004 equiv), and isophthalic acid (33 mg, 0.2 mmol, 0.1 equiv) were then added. The reaction tube was sealed, evacuated and back-filled with nitrogen (3×), and gradually heated to 132° C. Heating was continued for 2 hours, after which time the reaction mixture was cooled to ambient room temperature. Tridecane (internal standard, 490 microliters, 2 0 mmol) and diethyl ether (10 mL) were added and the tube was sonicated for 5 minutes to dissolve all solids. An aliquot (ca. 0.2 mL) of the resulting homogeneous solution was diluted with diethyl ether (1 mL) and shaken with aqueous NaOH (2N, 5 mL). An aliquot of the top ethereal layer (ca. 0.2 mL) was passed through a short plug of silica and further eluted with diethyl ether (2 mL). The resulting solution was analyzed by gas chromatography to determine olefin yield and alpha selectivity, the results provided in Tables 5 and 6

TABLE 5

Initial acid additive screening experiments

| Entry | Additive (equivalent) | % Yield$^a$ | % Alpha Olefin$^a$ |
|---|---|---|---|
| 1 | none | 10 | >99 |
| 2 | lauric acid | 48 | 80 |
| 3 | benzoic acid (1) | 85 | 46 |

$^a$Determined by gas chromatography with tridecane as internal standard

TABLE 6

Acid additive screening experiments

| Entry | Acid | Acid Loading | % Yield$^a$ | % Alpha Olefin$^a$ |
|---|---|---|---|---|
| 0 | none | — | 10 | 100 |
| 1 | benzoic acid (CO$_2$H) | A. 10 mol % B. 1 mol % | 67 22 | 72 93 |
| 2 | phthalic acid (1,2-(CO$_2$H)$_2$) | A. 10 mol % B. 1 mol % | 66 12 | 66 98 |
| 3 | isophthalic acid (1,3-(CO$_2$H)$_2$) | A. 10 mol % B. 1 mol % | 55 28 | 80 91 |
| 4 | terephthalic acid (1,4-(CO$_2$H)$_2$) | A. 10 mol % B. 1 mol % | 18 38 | 93 87 |
| 5 | 1,3,5-benzenetricarboxylic acid | A. 10 mol % B. 1 mol % | 51 27 | 82 92 |

TABLE 6-continued

Acid additive screening experiments

| Entry | Acid | Acid Loading | % Yield[a] | % Alpha Olefin[a] |
|---|---|---|---|---|
| 6 | HO2C-C6H3(CO2H)-CO2H (benzene-1,2,4-tricarboxylic acid) | A. 10 mol %<br>B. 1 mol % | 21<br>39 | 93<br>87 |
| 7 | 2-hydroxybenzoic acid (salicylic acid) | A. 10 mol %<br>B. 1 mol % | 36<br>14 | 86<br>96 |
| 8 | 2-benzoylbenzoic acid | A. 10 mol %<br>B. 1 mol % | 36<br>21 | 89<br>94 |
| 9 | p-TsOH·H2O | A. 10 mol %<br>B. 1 mol % | 26<br>96 | 26<br>20 |

[a]Determined by gas chromatography with tridecane as internal standard

Example 2.6

Phenol Additive Screen

Screening experiments testing the effects of phenols were done according to the following scheme, with the results presented in Table 7.

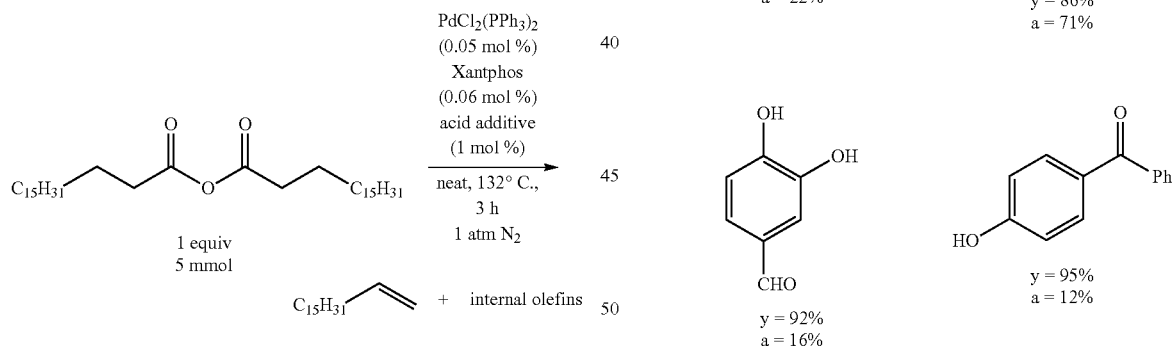

TABLE 7

Initial phenol additive screening experiments[a]

pentafluorophenol: y = 68%, a = 93% pentachlorophenol: y = 0

TABLE 7-continued

Initial phenol additive screening experiments[a]

hydroquinone: y = 60%, a = 93%

2-hydroxybenzophenone: y = 61%, a = 93% methyl 2-hydroxy-5-(methoxycarbonyl) substituted phenol: y = 40%, a = 97% dimethyl 2-hydroxyisophthalate: y = 30%, a = 98% methyl 3,4,5-trihydroxybenzoate: y = 94%, a = 22%

2,2'-biphenol: y = 86%, a = 71%

3,4-dihydroxybenzaldehyde: y = 92%, a = 16%

4-hydroxybenzophenone: y = 95%, a = 12% salicylamide: y = 91%, a = 40%

3,3'-di-t-butyl-5,5',6,6'-tetramethyl-2,2'-biphenol: y = 94%, a = 39%

TABLE 7-continued

Initial phenol additive screening experiments[a]

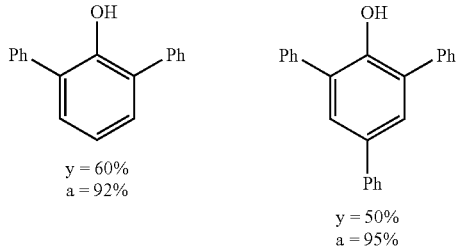

y = 60%
a = 92% y = 50%
a = 95%

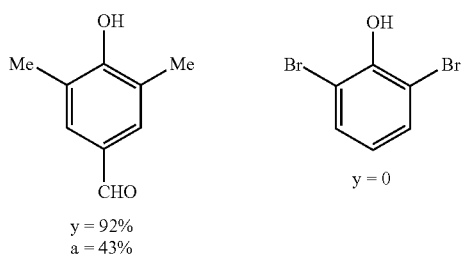

y = 92%
a = 43% y = 0 y = 93%
a = 35% y = 95%
a = 24%

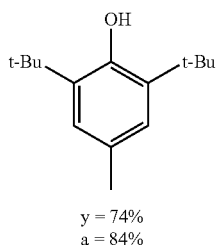 [SMILES: Cc1cc(C(C)(C)C)c(O)c(C(C)(C)C)c1]

y = 74%
a = 84%

[a]y is the yield; a is the proportion of Alpha olefin

Example 2.7

Base Additive Screen

Screening experiments testing the effects of bases were done, with the results presented in Table 8.

TABLE 8

Effect of amines on yields and selectivity

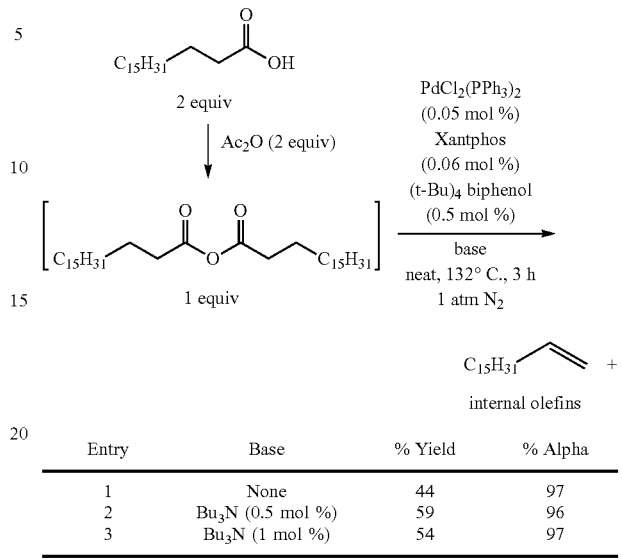

| Entry | Base | % Yield | % Alpha |
|---|---|---|---|
| 1 | None | 44 | 97 |
| 2 | Bu$_3$N (0.5 mol %) | 59 | 96 |
| 3 | Bu$_3$N (1 mol %) | 54 | 97 |

Example 2.8

Base Additive Screen

Additional screening experiments testing the effects of bases were done according to the following scheme, with the results presented in Table 9. In these experiments, the mixed anhydride was synthesized by treating palmitic acid with benzoyl chloride in the presence of triethylamine. The product was a mixture of the desired mixed anhydride and two symmetrical anhydrides of each acid that result from disproportionation.

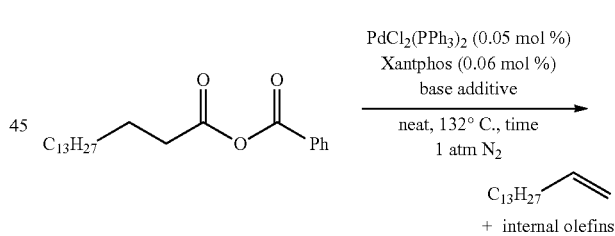

TABLE 9

Initial base additive screening experiments
(with mixed anhydride as substrate)

| Entry | Additive (mol %) | Time | % Yield[a] | % Alpha[a] |
|---|---|---|---|---|
| 1 | None | 3 hours | 81 | 41 |
| 2 | Bu$_3$N (1) | 3 hours | 73 | 84 |
| 3 | Bu$_3$N (1)/PEG 5000 (10) | 3 hours | 69 | 84 |
| 4 | Bu$_3$N (1)/NMP (10) | 3 hours | 68 | 81 |
| 5 | Bu$_3$N (1)/diglyme (10) | 3 hours | 70 | 79 |
| 6 | Bu$_3$N (1)/VP (1) | 3 hours | 64 | 86 |
| 7[b] | Bu$_3$N (2) | 3 hours | 58 | 93 |
| 8 | Cy$_2$NH (1) | 3 hours | 66 | 75 |
| 9 | PhCO$_2$Na (0.2) | 3 hours | 56 | 92 |
| 10 | BnNMe$_2$ (1) | 3 hours | 78 | 74 |
| 11 | i-Pr$_2$Net (1) | 3 hours | 80 | 79 |

TABLE 9-continued

Initial base additive screening experiments
(with mixed anhydride as substrate)

| Entry | Additive (mol %) | Time | % Yield[a] | % Alpha[a] |
|---|---|---|---|---|
| 12 | i-Pr$_2$Net (1) | 2 hours | 60 | 89 |
| 13 | TMG (1) | 2 hours | 58 | 93 |
| 14 | i-Pr$_2$Net (2) | 3 hours | 64 | 88 |
| 15 | TMG (2) | 3 hours | 68[c] | 91 |
| 16 | TMG (2)/DMAP (0.1) | 3 hours | 54 | 92 |
| 17 | TMG (2) | 2.5 hours | 56 | 95 |
| 18 | TMG (2)/Et$_4$NCl (1) | 3 hours | 74 | 67 |
| 19 | Barton's base (2) | 3 hours | 43 | 97 |
| 20 | Barton's base (1) | 3 hours | 55 | 92 |
| 21[d] | PhCO$_2$Li (0.5) | 3 hours | 78 | 81 |
| 22[d] | PhCO$_2$Li (1) | 3 hours | 72 | 84 |
| 23 | PhCO$_2$Li (1)/BHT (1) | 3 hours | 78 | 67 |
| 24 | PhCO$_2$Li (1)/BnOH (1) | 3 hours | 71 | 73 |
| 25[d] | TMG (4) | 3 hours | 69 | 62 |
| 26[d] | TMG (4) | 11 hours | 78 | 66 |
| 27[d] | Bu$_3$N (10) | 11 hours | 85 | 60 |
| 28[d] | Pr$_3$N (40) | 8 hours | 55 | 78 |
| 29[e] | TMG (2) | 3 hours | 60 | 88 |

[a]Determined by $^1$H NMR
[b]Added in portions (1 mol % at t = 0 and 1 mol % at t = 2 h)
[c]62% isolated yield
[d]5 mmol scale
[e]Reproduction of entry 15

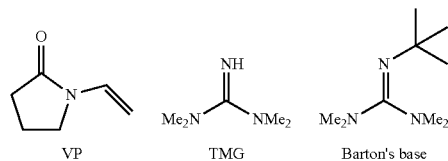

VP    TMG    Barton's base

Example 2.9

Effects of Simultaneous Distillation on Yield and Selectivity

In order to test the effect on selectivity by removing the olefin product before double bond migration, a series of experiments were done under continuous distillation. Experiments were conducted according to the following scheme, with the results presented in Table 10.

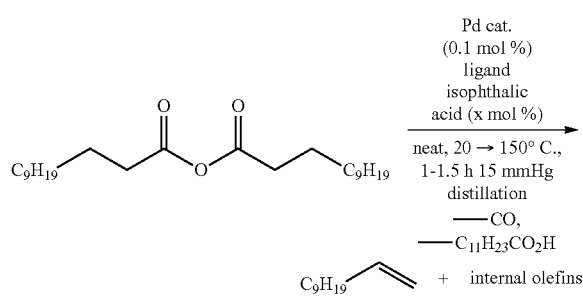

TABLE 10

Effects of simultaneous distillation on yield and selectivity

| Entry | Pd Catalyst | Ligand (mol %) | x (mol %) | % Yield[a] | % Alpha[a] |
|---|---|---|---|---|---|
| 1 | PdCl$_2$(nbd) | Xantphos (0.2) | 10 | 85 | 91 |
| 2 | PdCl$_2$(nbd) | Xantphos (0.2) | 5 | 85 | 92 |
| 3 | PdCl$_2$(PPh$_3$)$_2$ | Xantphos (0.12) | 5 | 80 | 98 |

[a] Determined by gas chromatography with tridecane as internal standard

When the decarbonylation was conducted at 150° C. under 15 mm Hg vacuum, the olefin products was isolated in 85% yield and about 90% alpha selectivity (Table 10, entries 1 and 2). Use of PdCl$_2$(PPh$_3$)$_3$ with slight stoichiometric excess of Xantphos, the alpha selectivity was further increased to 98%.

Example 2.10

Using Lauric-Benzoic Mixed Anhydrides as Substrates

A series of experiments were conducted activating a fatty acid substrate by forming a mixed anhydride with another readily recoverable acid. Acylation of lauric acid with benzoyl chloride in the presence of triethylamine produced a mixture of lauric-benzoic mixed anhydride (MA), lauric anhydride (LA), and benzoic anhydride (BA) in 69:18:13 ratio and greater than 90% yield. Decarbonylation of this mixture of anhydrides proceeded smoothly. The experiments were conducted according to the following scheme and procedure, with the results presented in Table 11.

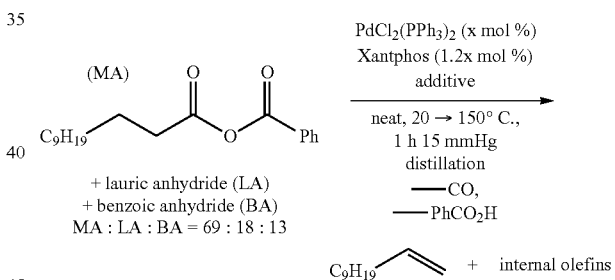

Representative Procedure (Table 11, entry 4): A 10-mL round-bottomed flask equipped with a magnetic stirbar was charged with lauric-benzoic mixed anhydride (6.08 g, 20 mmol, 1 equiv), PdCl$_2$(PPh$_3$)$_2$ (7 mg, 0.001 mmol, 0.0005 equiv), Xantphos (6.9 mg, 0.0012 mmol, 0.0006 equiv), and sodium benzoate (2.8 mg, 0.02 mmol, 0.001 equiv). A vacuum-jacketed short path distillation head equipped with a 25-mL round-bottomed flask was fitted to the reaction flask and the system was evacuated and back-filled with nitrogen (3×) and then held at 15 mm Hg vacuum. The receiving flask was cooled in an ice bath, and the reaction flask was gradually heated to 132° C. Heating was continued for 2 hours, after which the reaction mixture was allowed to cool to ambient room temperature. Tridecane (internal standard, 490 microliters, 2.0 mmol) and diethyl ether (10 mL) were added and the tube was sonicated for 5 minutes to dissolve all solids. An aliquot (ca. 0.2 mL) of the resulting homogeneous solution was diluted with diethyl ether (1 mL) and shaken with aqueous NaOH (2N, 5 mL). An aliquot of the top ethereal layer (ca. 0.2 mL) was passed through a short plug of silica and further eluted with diethyl ether (2 mL).

The resulting solution was analyzed by gas chromatography to determine olefin yield and alpha selectivity, the results provided in Table 11.

TABLE 11

Using lauric-benzoic mixed anhydrides as substrates

| Entry | Scale (mmol) | x (mol %) | Additive (mol %) | % Yield [a] | % Alpha [a] |
|---|---|---|---|---|---|
| 1 | 10 | 0.1 | — | 63 | 98 |
| 2 | 20 | 0.05 | — | 67 | 94 |
| 3 | 20 | 0.05 | DMAP (0.1) | 74 | 95 |
| 4 | 20 | 0.05 | PhCO$_2$Na (0.1) | 67 | 98 |
| 5 | 100 [b] | 0.05 | PhCO$_2$Na (0.5) | 66 | 91 |

[a] Determined by gas chromatography with tridecane as internal standard
[b] Conducted neat, 20 → 150° C., 1.4 hr, 17 mm Hg distillation in presence of LiCl (1 mol %)

Example 3

General Procedure for Optimization Reactions

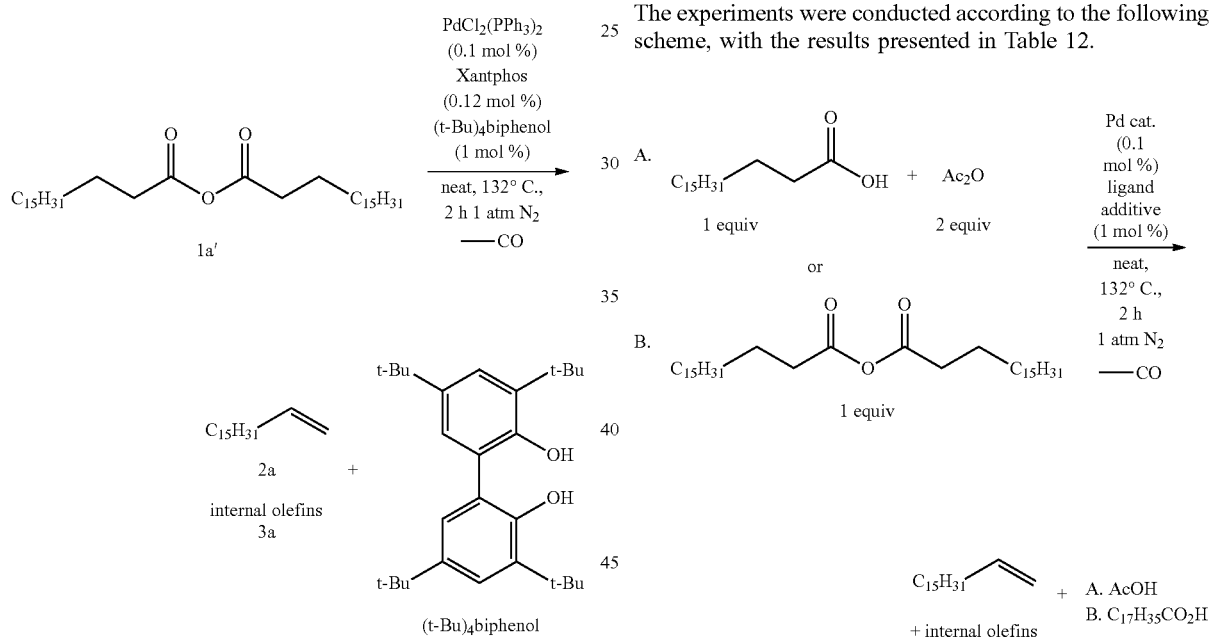

The procedure for the representative reaction (Table 12, entry 12) is shown as follows. To a 20×150 mm Kimble glass tube equipped with a magnetic stir bar was added PdCl$_2$(PPh$_3$)$_2$ (0.005 mmol, 0.1 mol %), Xantphos (0.006 mmol, 0.12 mol %), (t-Bu)$_4$biphenol (0.05 mmol, 1 mol %), and stearic anhydride 1a' (5 mmol, 1 equiv). The tube was sealed with a rubber septum, evacuated and refilled with N$_2$ (×3), and placed in a preheated 132° C. oil bath and stirred for 2 h. The oil bath was removed, and methyl benzoate (internal standard, 5 mmol, 1 equiv) was added and the resulting mixture stirred for 1 min. An aliquot of the crude mixture was taken by pipette and analyzed by $^1$H NMR.

Example 3.1

Effects of Catalyst, Ligand, and Additive

A series of experiments were conducted to compare the effects of generating precursor anhydrides in situ vs. adding the precursor anhydrides directly, and to explore a range of potential additives on the relative reactivity and selectivity. The experiments were conducted according to the following scheme, with the results presented in Table 12.

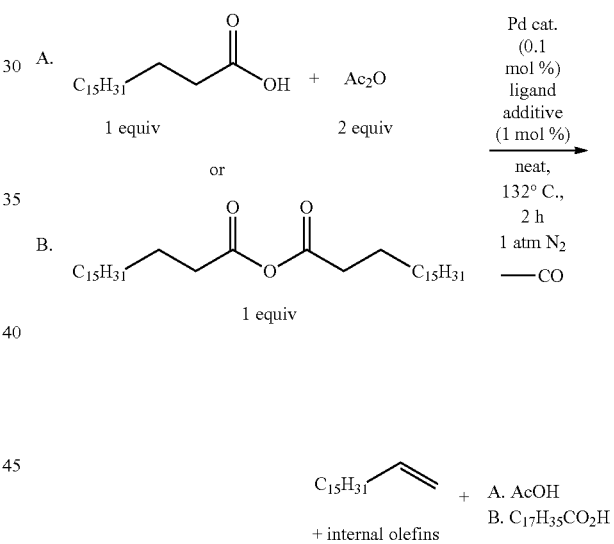

TABLE 12

Effects of Catalyst, Ligand, and Additive

| Entry | Scheme | Pd Catalyst | Ligand (mol %) | Additive | % Yield[a] | % Alpha[a] | % Y * A[b] |
|---|---|---|---|---|---|---|---|
| 1 | A | PdCl$_2$(nbd) | PPh$_3$ (0.8) | — | 0 | — | 0 |
| 2 | A | PdCl$_2$(nbd) | Dppp (0.4) | — | 0 | — | 0 |
| 3 | A | PdCl$_2$(nbd) | DPEphos (0.4) | — | 43 | 59 | 25 |
| 4 | A | PdCl$_2$(nbd) | Xantphos (0.4) | — | 60 | 55 | 33 |
| 5 | B | PdCl$_2$(nbd) | Xantphos (0.4) | — | 12 | 100 | 12 |
| 6 | B | PdCl$_2$(nbd) | Xantphos (0.4) | Isophthalic acid | 22 | 96 | 21 |
| 7 | B | PdCl$_2$(nbd) | Xantphos (0.12) | Isophthalic acid | 92 | 31 | 29 |
| 8 | B | PdCl$_2$(PPh$_3$)$_2$ | Xantphos (0.12) | Isophthalic acid | 90 | 54 | 49 |
| 9 | B | PdCl$_2$(PPh$_3$)$_2$ | Xantphos (0.12) | p-TsOH·H$_2$O | 86 | 5 | 4 |
| 10 | B | PdCl$_2$(PPh$_3$)$_2$ | Xantphos (0.12) | salicylamide | 60 | 90 | 54 |

TABLE 12-continued

Effects of Catalyst, Ligand, and Additive

| Entry | Scheme | Pd Catalyst | Ligand (mol %) | Additive | % Yield[a] | % Alpha[a] | % Y * A[b] |
|---|---|---|---|---|---|---|---|
| 11 | B | PdCl$_2$(PPh$_3$)$_2$ | Xantphos (0.12) | 2,2'-biphenol | 59 | 91 | 54 |
| 12 | B | PdCl$_2$(PPh$_3$)$_2$ | Xantphos (0.12) | (${}^t$-Bu)$_4$biphenol | 84 | 70 | 59 |

[a] Determined by gas chromatography with tridecane as internal standard
[b] Y × A = Yield × Alpha

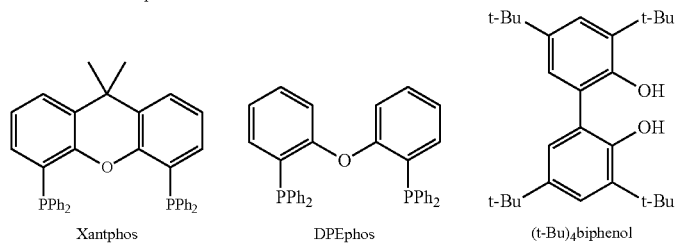

Xantphos    DPEphos    (t-Bu)$_4$biphenol

Example 3.2

Effects of Batchwise Addition of Acetic Anhydride

Control experiments involving pre-formed stearic anhydride as substrate showed that the buildup of acid in the reaction mixture was responsible for olefin isomerization and erosion of alpha selectivity. A series of experiments were conducted to compare the effects of adding the sacrificial anhydrides portionwise, over a period of time. The experiments were conducted according to the following scheme, with the results presented in Table 13. These experiments clearly show the remarkable result that the more frequently the sacrificial anhydride is added to dehydrate the precursor anhydride acid (stearic acid in this case), the higher the alpha selectivity.

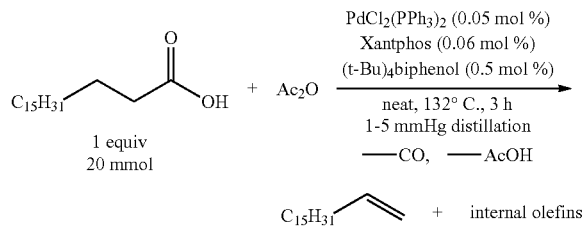

TABLE 13

Effects of Portionwise Addition of Acetic Anhydride

| Entry | Equivalents of Ac$_2$O | % Yield[a] | % Alpha[a] |
|---|---|---|---|
| 1 | 1 + 0.5 (once every 1.5 hrs) | 69 | 62 |
| 2 | 1 + 0.5 + 0.25 (once every hour) | 67 | 86 |
| 3 | 1 + 0.14 + 0.12 + 0.1 + 0.09 + 0.08 (once every half hour) | 68 (67) | 89 |

[a] Determined by gas chromatography with tridecane as internal standard

Example 3.3

Substrate Scope Studies

With the optimized conditions in hand, experiments of decarbonylative dehydration of a variety of fatty acid substrates were conducted (Table 14). Common saturated fatty acids with carbon numbers from 12 to 18 all gave the corresponding olefin in good yield and high alpha selectivity (entries 1-4). In particular, volatile olefins were formed in exceptionally high selectivity (entries 3 and 4). Terminally functionalized fatty acids were also competent substrates, and functional groups such as esters, chlorides, imides, silyl ethers, ketones, terminal olefins, and substituted aromatics were all well tolerated (entries 5-13). Notably, allylbenzene derivative was formed in 91% alpha selectivity (entry 11), considering the significant thermodynamic driving force for isomerization into conjugation with the aromatic ring. Carboxylic acids with alpha- or beta-substituents were considerably less reactive (entries 14 and 15). Nevertheless, catalyst turnovers around 400 could be achieved for these substrates. Comparing with previous reports by Miller and Kraus, our reaction has a much broader scope, does not require distillation of olefin to maintain high selectivity, and is compatible with various heteroatom functional groups.

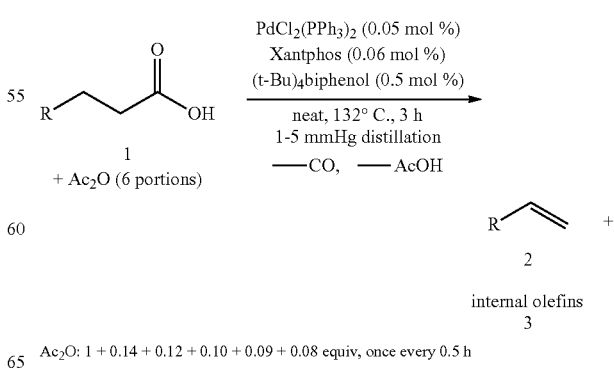

Ac$_2$O: 1 + 0.14 + 0.12 + 0.10 + 0.09 + 0.08 equiv, once every 0.5 h

TABLE 14
Substrate Scope Studies (20 mmol scale).
| Entry | Substrate | Product | % Yield[a] | Turnover No | % Alpha[b] |
|---|---|---|---|---|---|
| 1 | 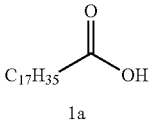 1a | 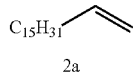 2a | 67 | 1340 | 89 |
| 2 | 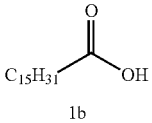 1b | 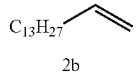 2b | 41 | 820 | 97 |
| 3 | 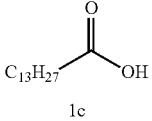 1c | 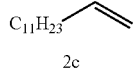 2c | 65 | 1300 | 99 |
| 4 | 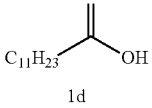 1d | 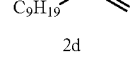 2d | 73 | 1460 | 99 |
| 5[c,d] | 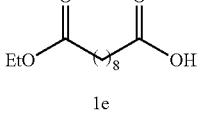 1e | 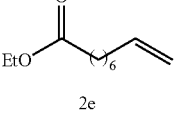 2e | 63 | 1260 | 98 |
| 6[c] | 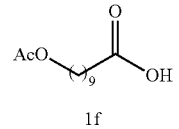 1f | 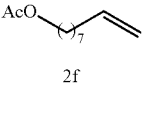 2f | 67 | 1340 | 96 |
| 7[c] | 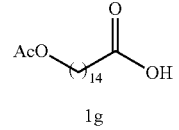 1g | 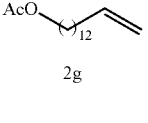 2g | 60 | 1200 | 89 |
| 8 | 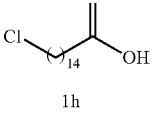 1h | 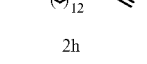 2h | 75 | 1500 | 86 |
| 9 | 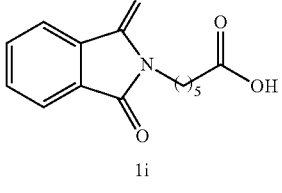 1i | 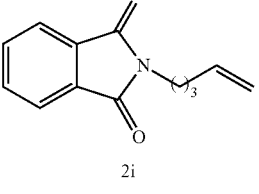 2i | 75 | 1520 | 83 |
| 10 | 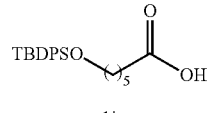 1j | 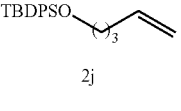 2j | 64 | 1280 | 80 |

TABLE 14-continued

Substrate Scope Studies (20 mmol scale).

| Entry | Substrate | Product | % Yield[a] | Turnover No | % Alpha[b] |
|---|---|---|---|---|---|
| 11 | 1k | 2k | 80 | 1600 | 91 |
| 12 | 1l | 2l | 49 | 980 | 88 |
| 13 | 1m | 2m | 59 | 1180 | 87 |
| 14[e] | 1n | 2n | 20<br>80[g] | 400<br>320[g] | f<br>g |
| 15 | 1o | 2o | 19 | 380 | 100 |
| 16 | 1p' | 3p | 71 | 71 | h |

[a] Isolated yield (column chromatorgraphy).
[b] Determined by 1H NMR.
[c] Purified by distillation.
[d] 18.5 mmol scale.
[e] PdCl$_2$(nbd) (0.05 mol %), PPh$_3$ (0.05 mol %), 1.5 h, 3 batches of Ac$_2$O.
[f] Single isomer observed
[g] PdCl$_2$(PPh$_3$)$_2$ (0.25 mol %), Xantphos (0.3 mol %), (t-Bu)$_4$biphenol (1 mol %), 2n:3n = 49:51
[h] 2-methyldecanoic anhydride (10 mmol), no Ac$_2$O, PdCl$_2$(nbd) (1 mol %), Xantphos (1.1 mol %), saliylamide (2 mol %), 160° C., 10 mm Hg distillation, 10 hr

Example 3.4

Large Scale Decarbonylative Dehydration of Stearic Acid and 10-Acetoxydecanoic Acid

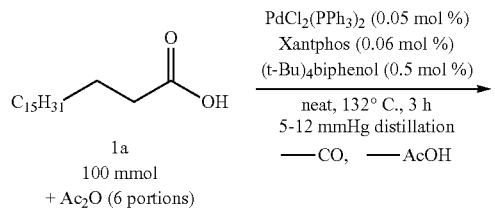

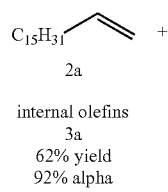

internal olefins
3a
62% yield
92% alpha

Ac$_2$O: 1 + 0.14 + 0.12 + 0.10 + 0.09 + 0.08 equiv, once every 0.5 h

-continued

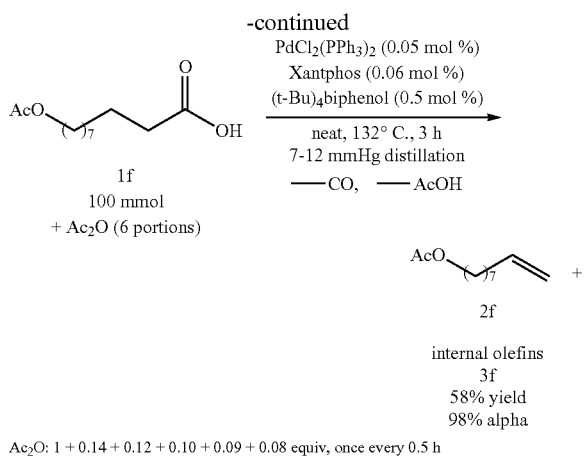

1f
100 mmol
+ Ac₂O (6 portions)

internal olefins
3f
58% yield
98% alpha

Ac₂O: 1 + 0.14 + 0.12 + 0.10 + 0.09 + 0.08 equiv, once every 0.5 h

Since this process required no solvent and low catalyst loading, it could be easily scaled up. In a laboratory setting, a 100 mmol scale decarbonylative dehydration was easily carried out in a 100 mL round-bottom flask. The alpha selectivity was better at a larger scale (94% at 100 mmol vs. 89% at 20 mmol). When the olefin is sufficiently volatile, it was distilled out together with the acetic acid (Table 14, Substrate Scope, entries 3-5, 9, and 11). Although distillation of olefin was not necessary to maintaining high selectivity, it was convenient to do so in case of volatile olefins.

Example 3.5

General Procedure for Preparative Pd-Catalyzed Decarbonylative Dehydration

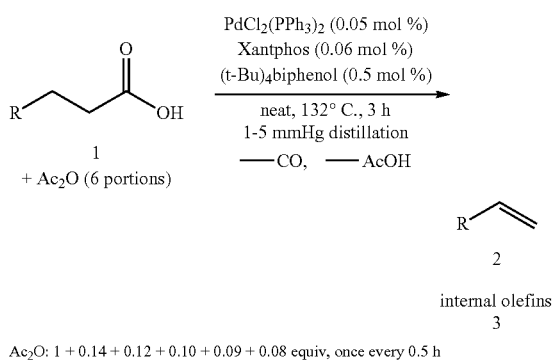

Ac₂O: 1 + 0.14 + 0.12 + 0.10 + 0.09 + 0.08 equiv, once every 0.5 h

A 15 mL round-bottom flask was charged with PdCl₂(PPh₃)₂ (0.01 mmol, 0.05 mol %), Xantphos (0.012 mmol, 0.06 mol %), (t-Bu)₄biphenol (0.1 mmol, 0.5 mol %), and fatty acid substrate (20 mmol, 1 equiv). The flask was equipped with a distillation head and a 25 mL round-bottom receiving flask. The closed system was connected to a vacuum manifold, equipped with a needle valve and a digital vacuum gauge. The system was evacuated and refilled with N₂ (×3), and the first portion of acetic anhydride (20 mmol, 1 equiv) was added via syringe through the septum that seals the top of the distillation head. The flask was lowered into a 20° C. oil bath and gradually heated to 132° C. in 23 minutes (When the reaction was performed at 100 mmol scale with high-melting substrates such as stearic acid, the reaction flask was first heated to 85° C. until all solid melted, and then to 132° C. Overall heating time from 20 to 132° C. was approximately 40 min) When oil bath temperature rose to 122° C., the needle valve was closed, switched to vacuum, and the needle valve carefully and slowly opened to allow distillation of acetic acid into a receiving flask, which was cooled to −78° C. When the oil bath temperature reached 130° C., time was recorded as t=0. After distillation ceased (about t=3 min), the needle valve was opened fully and a vacuum of 1-5 mmHg was drawn. At t=30 min, the system was refilled with N₂, and the second portion of acetic anhydride (2.8 mmol, 0.14 equiv) was added via syringe. The system was then gradually (t=35 min) resubjected to a vacuum of 1-5 mmHg. Acetic anhydride was added as follows (0.12, 0.10, 0.09. 0.08 equiv) in the same manner every 30 min. The reaction was stopped at t=3 h and allowed to cool to ambient temperature. The residual reaction mixture was purified by flash chromatography. If it contained solids, it was suction-filtered first and the solids washed with hexanes, and the filtrate was concentrated and purified by chromatography. In cases where the product was distilled together with acetic acid, the distillate was added dropwise to a saturated NaHCO₃ solution, stirred for 30 min, and the resulting mixture was extracted with dichloromethane (30 mL×3). The combined extracts were dried over Na₂SO₄, filtered and concentrated. The crude product was then subjected to flash chromatography or distillation to afford the olefin in pure form.

Example 4

Spectroscopic Data for Compounds in Table 14

The fatty acids of entries 1-4 and 11 are commercially available. Carboxylic acids of entry 5 (Regourd, J, et al., *J. Med. Chem.* 2007, 50, 1528-1536), of entry 6 (Kazlauskas, R., et al., *Aust. J. Chem.* 1982, 35, 113-120), of entry 7 (Guenin, E., et al., *Eur. J. Org. Chem.* 2007, 3380-3391.), of entry 15 (Oppolzer, W., et al., *J. Org. Chem.* 2001, 66, 4766-4770), of entry 9 (Ohishi, T., et al., *Angew. Chem., Int. Ed.* 2011, 50, 8114-8117), 11 (Kaiser, R., et al., *Helv. Chim. Acta* 1978, 61, 2671-2680), and of entry 12 (Wang, Z., et al., *J. Am. Chem. Soc.* 2012, 134, 4258-4263) are known compounds and prepared according to the referenced literature methods.

15-Chloropentadecanoic acid (entry 7)

$^1$H NMR (500 MHz, CDCl₃) δ 3.52 (t, J=6.8 Hz, 2H), 2.34 (t, J=7.5 Hz, 2H), 1.79-1.73 (m, 2H), 1.62 (p, J=7.5 Hz, 2H), 1.46-1.20 (m, 20H); $^{13}$C NMR (126 MHz, CDCl₃) δ 180.6, 45.3, 34.2, 32.8, 29.7, 29.7, 29.7, 29.7, 29.6, 29.6, 29.4, 29.2, 29.0, 27.0, 24.8; IR (Neat Film) 2916, 2848, 1701, 1462, 1410, 1302, 943, 721 cm$^{-1}$; HRMS (NMM: ESI-APCI−) m/z calc'd for C₁₅H₂₈O₂Cl [M−H]$^-$: 275.1783, found 275.1794.

3-Methylpentadecanoic acid (entry 13)

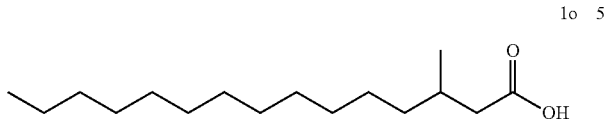

¹H NMR (500 MHz, CDCl₃) δ 2.35 (dd, J=15.0, 5.9 Hz, 1H), 2.14 (dd, J=15.0, 8.2 Hz, 1H), 2.01-1.90 (m, 1H), 1.38-1.15 (m, 22H), 0.96 (d, J=6.7 Hz, 3H), 0.88 (t, J=6.9 Hz, 3H); ¹³C NMR (126 MHz, CDCl₃) δ 180.1, 41.8, 36.8, 32.1, 30.3, 29.9, 29.8, 29.8, 29.8, 29.8, 29.8, 29.5, 27.0, 22.9, 19.8, 14.3; IR (Neat Film) 2914, 2852, 1701, 1473, 1410, 1300, 1151, 1123, 954, 715; HRMS (NMM: ESI-APCI−) m/z calc'd for $C_{16}H_{31}O_2$ [M—H]⁻: 255.2330, found 255.2328.

1-Heptadecene (entry 1)

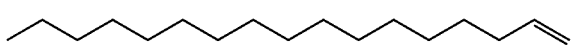

¹H NMR (500 MHz, CDCl₃) δ 5.82 (ddt, J=16.9, 10.2, 6.7 Hz, 1H), 5.07-4.86 (m, 2H), 2.11-1.98 (m, 2H), 1.49-1.08 (m, 26H), 0.88 (t, J=6.9 Hz, 3H); ¹³C NMR (126 MHz, CDCl₃) δ 139.4, 114.2, 34.0, 32.1, 29.9, 29.8, 29.8, 29.8, 29.7, 29.7, 29.5, 29.5, 29.4, 29.3, 29.1, 22.9, 14.3. See, Barton, D. H. R., et al., *Tetrahedron* 1991, 47, 7091-7108

1-Pentadecene (entry 2)

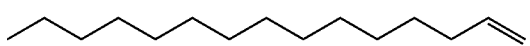

¹H NMR (500 MHz, CDCl₃) δ 5.82 (ddt, J=16.9, 10.2, 6.7 Hz, 1H), 5.07-4.85 (m, 2H), 2.11-1.97 (m, 2H), 1.46-1.08 (m, 22H), 0.88 (t, J=6.9 Hz, 3H); ¹³C NMR (126 MHz, CDCl₃) δ 139.4, 114.2, 34.0, 32.1, 29.9, 29.9, 29.8, 29.8, 29.8, 29.7, 29.6, 29.3, 29.1, 22.9, 14.3. See, Burns, D. H., et al., *J. Am. Chem. Soc.* 1997, 119, 2125-2133

1-Tridecene (entry 3)

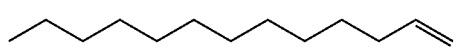

¹H NMR (500 MHz, CDCl₃) δ 5.82 (ddt, J=17.0, 10.1, 6.7 Hz, 1H), 5.09-4.83 (m, 2H), 2.11-1.97 (m, 2H), 1.48-1.11 (m, 18H), 0.88 (t, J=6.9 Hz, 3H); ¹³C NMR (126 MHz, CDCl₃) δ 139.4, 114.2, 34.0, 32.1, 29.8, 29.8, 29.8, 29.7, 29.5, 29.3, 29.1, 22.9, 14.3. See, Rojas, G., et al., *J. Org. Chem.* 2008, 73, 4962-4970

1-Undecene (entry 4)

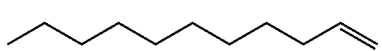

¹H NMR (500 MHz, CDCl₃) δ 5.82 (ddt, J=16.9, 10.2, 6.7 Hz, 1H), 5.08-4.84 (m, 2H), 2.11-1.98 (m, 2H), 1.47-1.09 (m, 14H), 0.88 (t, J=6.9 Hz, 3H); ¹³C NMR (126 MHz, CDCl₃) δ 139.4, 114.2, 34.0, 32.1, 29.8, 29.7, 29.5, 29.3, 29.1, 22.8, 14.3. See, Vijai Kumar Reddy, T., et al., *Bioorg. Med. Chem. Lett.* 2012, 22, 4678-4680

Ethyl non-8-enoate (entry 5)

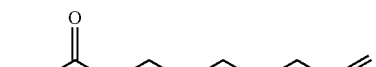

¹H NMR (500 MHz, CDCl₃) δ 5.80 (ddt, J=16.6, 9.9, 6.8 Hz, 1H), 5.07-4.87 (m, 2H), 4.12 (q, J=7.2 Hz, 2H), 2.28 (t, J=7.5 Hz, 2H), 2.10-1.98 (m, 2H), 1.69-1.54 (m, 2H), 1.46-1.28 (m, 6H), 1.25 (t, J=7.1 Hz, 3H); ¹³C NMR (126 MHz, CDCl₃) δ 174.0, 139.1, 114.4, 60.3, 34.5, 33.8, 29.1, 28.8, 28.8, 25.0, 14.4. See, Ravu, V. R., et al., *Eur. J. Org. Chem.* 2011, 463-468

Non-8-en-1-yl acetate (entry 6)

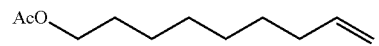

¹H NMR (500 MHz, CDCl₃) δ 5.80 (ddt, J=16.9, 10.2, 6.7 Hz, 1H), 5.07-4.87 (m, 2H), 4.05 (t, J=6.8 Hz, 2H), 2.14-1.94 (m, 5H), 1.70-1.52 (m, 2H), 1.47-1.18 (m, 8H); ¹³C NMR (126 MHz, CDCl₃) δ 171.4, 139.2, 114.4, 64.8, 33.9, 29.2, 29.1, 29.0, 28.7, 26.0, 21.2. See, Mori, K., *Tetrahedron* 2009, 65, 3900-3909.

Tetradec-13-en-1-yl acetate (entry 7)

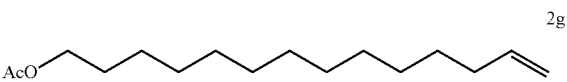 [SMILES: C=CCCCCCCCCCCCCOC(C)=O]

¹H NMR (500 MHz, CDCl₃) δ 5.81 (ddt, J=16.8, 10.1, 6.8 Hz, 1H), 5.08-4.86 (m, 2H), 4.05 (t, J=6.8 Hz, 2H), 2.11-1.98 (m, 5H), 1.69-1.53 (m, 2H), 1.45-1.09 (m, 18H); ¹³C NMR (126 MHz, CDCl₃) δ 171.4, 139.4, 114.2, 64.8, 34.0, 29.8, 29.7, 29.7, 29.6, 29.6, 29.4, 29.3, 29.1, 28.7, 26.0, 21.2. See, Lin, J., et al., *Synth. Commun.* 1995, 25, 3457-3461

14-Chlorotetradec-1-ene (entry 8)

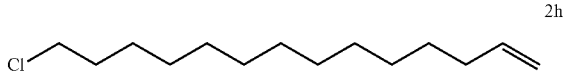

¹H NMR (500 MHz, CDCl₃) δ 5.81 (ddt, J=17.0, 10.2, 6.7 Hz, 1H), 5.07-4.86 (m, 2H), 3.53 (t, J=6.8 Hz, 2H), 2.11-1.98 (m, 2H), 1.77 (dt, J=14.5, 6.9 Hz, 2H), 1.50-1.10 (m, 18H); ¹³C NMR (126 MHz, CDCl₃) δ 139.4, 114.2, 45.3, 34.0, 32.8, 29.8, 29.7, 29.7, 29.6, 29.6, 29.3, 29.1, 29.0, 27.0; IR (Neat Film, NaCl) 3076, 2925, 2854, 1641, 1465, 1309, 993, 966, 909, 723 cm⁻¹; HRMS (FAB+) m/z calc'd for C₁₄H₂₇³⁵Cl [M]³⁰: 230.1801, found 230.1808.

2-(Pent-4-en-1-yl)isoindoline-1,3-dione (entry 9)

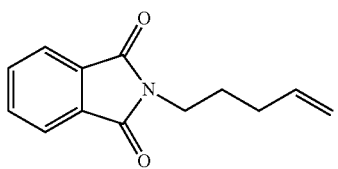

2i

¹H NMR (500 MHz, CDCl₃) δ 7.89-7.73 (m, 2H), 7.73-7.58 (m, 2H), 5.77 (ddt, J=16.9, 10.2, 6.6 Hz, 1H), 5.10-4.87 (m, 2H), 3.74-3.57 (m, 2H), 2.17-2.00 (m, 2H), 1.74 (p, J=7.5 Hz, 2H); ¹³C NMR (126 MHz, CDCl₃) δ 168.4, 137.3, 133.9, 132.2, 123.2, 115.3, 37.6, 31.0, 27.7. See, Whittaker, A. M., et al., *Org. Lett.* 2013, 15, 1112-1115.

tert-Butyl(pent-4-en-1-yloxy)diphenylsilane (entry 10)

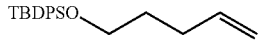

2j

¹H NMR (500 MHz, CDCl₃) δ 7.67 (dt, J=6.5, 1.5 Hz, 4H), 7.39 (dddd, J=14.4, 8.3, 6.0, 2.1 Hz, 6H), 5.80 (ddt, J=16.9, 10.2, 6.6 Hz, 1H), 5.09-4.87 (m, 2H), 3.68 (t, J=6.5 Hz, 2H), 2.15 (tdd, J=8.1, 6.8, 1.4 Hz, 2H), 1.73-1.60 (m, 2H), 1.05 (s, 9H); ¹³C NMR (126 MHz, CDCl₃) δ 138.7, 135.7, 134.2, 129.7, 127.7, 114.7, 63.4, 32.0, 30.2, 27.0, 19.4. See Dias, D. A., et al., *Org. Lett.* 2009, 11, 3694-3697.

1-Allyl-4-methoxybenzene (entry 11)

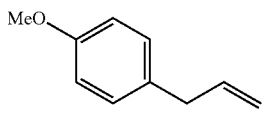

2k

¹H NMR (500 MHz, CDCl₃) δ 7.17-7.06 (m, 2H), 6.91-6.78 (m, 2H), 5.96 (ddt, J=16.8, 10.1, 6.7 Hz, 1H), 5.13-4.99 (m, 2H), 3.79 (s, 3H), 3.34 (d, J=6.7 Hz, 2H); ¹³C NMR (126 MHz, CDCl₃) δ 158.1, 138.0, 132.2, 129.6, 115.5, 113.9, 55.4, 39.5. See, Ackermann, L., et al., *Org. Lett.* 2010, 12, 2298-2301.

Tridec-12-en-2-one (entry 12)

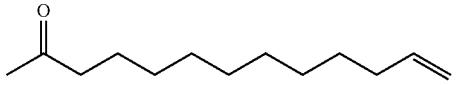

2l

¹H NMR (500 MHz, CDCl₃) δ 5.81 (ddt, J=16.9, 10.1, 6.7 Hz, 1H), 5.06-4.87 (m, 2H), 2.41 (t, J=7.5 Hz, 2H), 2.13 (s, 3H), 2.09-1.97 (m, 2H), 1.62-1.49 (m, 2H), 1.46-1.11 (m, 12H); ¹³C NMR (126 MHz, CDCl₃) δ 209.5, 139.3, 114.2, 43.9, 33.9, 30.0, 29.5, 29.5, 29.5, 29.3, 29.2, 29.0, 24.0. See Arbain, D., et al., *Aust. J. Chem.* 1990, 43, 1949-1952

Deca-1,9-diene (entry 11)

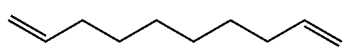

2m

¹H NMR (500 MHz, CDCl₃) δ 5.81 (ddt, J=17.0, 10.2, 6.7 Hz, 2H), 5.08-4.86 (m, 4H), 2.11-1.98 (m, 4H), 1.48-1.21 (m, 8H); ¹³C NMR (126 MHz, CDCl₃) δ 139.3, 114.3, 33.9, 29.1, 29.0. See Garwood, R. F., et al., *J. Chem. Soc., Perkin Trans. 1* 1973, 2714-2721.

(3,6-Dihydropyridin-1(2H)-yl)(phenyl)methanone (entry 14)

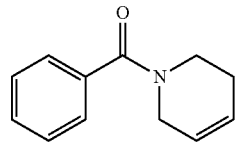

2n

¹H NMR (500 MHz, DMSO-d₆, 130° C.) δ 7.41 (ddd, J=24.3, 6.8, 3.4 Hz, 5H), 5.90-5.82 (m, 1H), 5.78-5.64 (m, 1H), 4.00 (p, J=2.8 Hz, 2H), 3.56 (t, J=5.8 Hz, 2H), 2.16 (dp, J=8.7, 3.2 Hz, 2H); ¹³C NMR (126 MHz, DMSO-d₆, 130° C.) δ 168.8, 136.1, 128.5, 127.5, 125.9, 124.6, 123.7, 43.4, 41.1, 24.3. See, Olofson, R. A., et al., *J. Org. Chem.* 1984, 49, 2795-2799.

(3,4-Dihydropyridin-1(2H)-yl)(phenyl)methanone (entry 14)

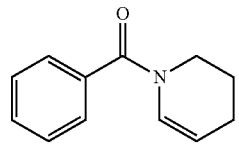

3n

¹H NMR (500 MHz, DMSO-d₆, 130° C.) δ 7.45 (tdd, J=6.0, 3.9, 2.4 Hz, 5H), 6.78-6.61 (m, 1H), 4.97 (dt, J=8.2, 3.9 Hz, 1H), 3.72-3.60 (m, 2H), 2.09 (tdd, J=6.2, 3.8, 2.0 Hz, 2H), 1.85 (p, J=6.1 Hz, 2H); ¹³C NMR (126 MHz, DMSO-d$_6$, 130° C.) δ 167.2, 135.0, 129.0, 127.5, 126.6, 125.6, 107.1, 42.0, 20.9, 20.8. See Gigant, N., et al., *Org. Lett.* 2013, 15, 278-281.

2-Methyltetradec-1-ene (entry 15)

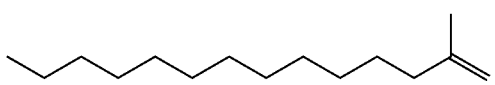

$^1$H NMR (500 MHz, CDCl$_3$) δ 4.72-4.63 (m, 2H), 2.00 (t, J=7.7 Hz, 2H), 1.71 (s, 3H), 1.47-1.11 (m, 20H), 0.88 (t, J=6.9 Hz, 3H); $^{13}$C NMR (126 MHz, CDCl$_3$) δ 146.5, 109.6, 38.0, 32.1, 29.9, 29.9, 29.8, 29.8, 29.7, 29.5, 29.5, 27.8, 22.9, 22.6, 14.3. See Pearlman, B. A., et al. *J. Org. Chem.* 1985, 50, 3625-3626.

(E)- and (Z)-2-decene (entry 16)

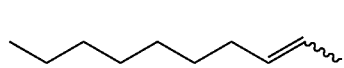

$^1$H NMR (500 MHz, CDCl$_3$) δ 5.48-5.35 (m, 2H), 2.07-1.93 (m, 2H), 1.64 (d, J=4.2 Hz, 3H, E-olefin), 1.60 (d, J=6.1 Hz, 3H, Z-olefin), 1.43-1.20 (m, 10H), 0.88 (t, J=6.6 Hz, 3H). See Yanagisawa, et al., *J. Am. Chem. Soc.* 1994, 116, 6130-6141.

Example 5

Procedure for Pheromone Synthesis by Ru-Catalyzed Cross Metathesis

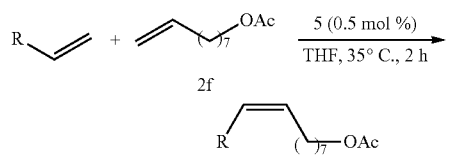

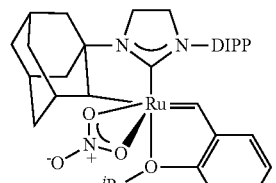

In a glovebox, a 20 mL vial was charged with 8-nonenyl acetate (2f, 1.0 mL, 4.8 mmol), 1-pentene or 1-hexene (6.0 mL, 48 mmol), and THF (2.6 mL). Ruthenium metathesis catalyst 5 (16 mg, 0.024 mmol, 0.5 mol %) was added and the reaction was stirred at 35° C. in an open vial for 2 hours. The vial was removed from the glovebox, quenched with ethyl vinyl ether (2.5 mL) and stirred for 30 minutes. The solvent was then removed in vacuo. The crude mixture was passed through a SiO$_2$ plug (hexane to 4% ethyl acetate in hexanes) to provide a mixture of unreacted 8-nonenyl acetate and pheromone 4. Pheromone 4 was isolated as the pure Z-isomer (>98% Z as determined by $^1$H NMR) by distillation using a Kugelrohr apparatus.

(Z)-dodec-8-en-1-yl acetate (4a)

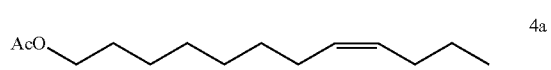

$^1$H NMR (500 MHz, CDCl$_3$) δ 5.35 (2H, m), 4.04 (2H, t, J=6.8 Hz), 2.04 (3H, s), 2.01 (4H, m), 1.61 (2H, m), 1.27-1.39 (10H, m), 0.89 (3H, t, J=7.4 Hz); $^{13}$C NMR (CDCl$_3$): δ 171.4, 130.1, 129.9, 64.8, 29.8, 29.4, 29.3 (2 C), 28.7, 27.3, 26.0, 23.0, 21.2, 14.0; HRMS (EI+) m/z calc'd for C$_{14}$H$_{27}$O$_2$ [M+H]$^+$: 227.2011, found 227.2012. See Rosebrugh, et al., *J. Am. Chem. Soc.* 2013, 135, 1276-1279.

(Z)-tridec-8-en-1-yl acetate (4b)

$^1$H NMR (500 MHz, CDCl$_3$) δ 5.34 (m, 2H), 4.05 (t, J=6.8 Hz, 2H), 2.00-2.04 (m, 7H), 1.60-1.63 (m, 2H), 1.29-1.36 (m, 12H), 0.88-0.91 (m, 3H); $^{13}$C NMR (126 MHz, CDCl$_3$) δ 171.4, 130.1, 129.9, 64.8, 32.1, 29.8, 29.3, 28.7, 27.3, 27.1, 26.0, 22.5, 21.2, 14.2; HRMS (FAB+) m/z calc'd for C$_{15}$H$_{29}$O$_2$ [M+H]$^+$: 241.2168, found 241.2167. See Rosebrugh, et al., *J. Am. Chem. Soc.* 2013, 135, 1276-1279.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method for forming an olefin product via decarbonylative dehydration of carboxylic acids or carboxylic acid anhydrides, said method comprising contacting:
   (a) a precursor carboxylic acid anhydride;
   (b) a palladium catalyst comprising a bidentate bis-phosphine ligand; and
   (c) an organic acid selected from the group consisting of substituted benzoic acids and substituted phenols;

said contacting done in a reaction mixture under conditions to form an olefin product with the concomitant formation and removal of CO and water from the reaction mixture;

wherein the bidentate bis-phosphine ligand comprises a structure of Formulae (I), (II), or (III);

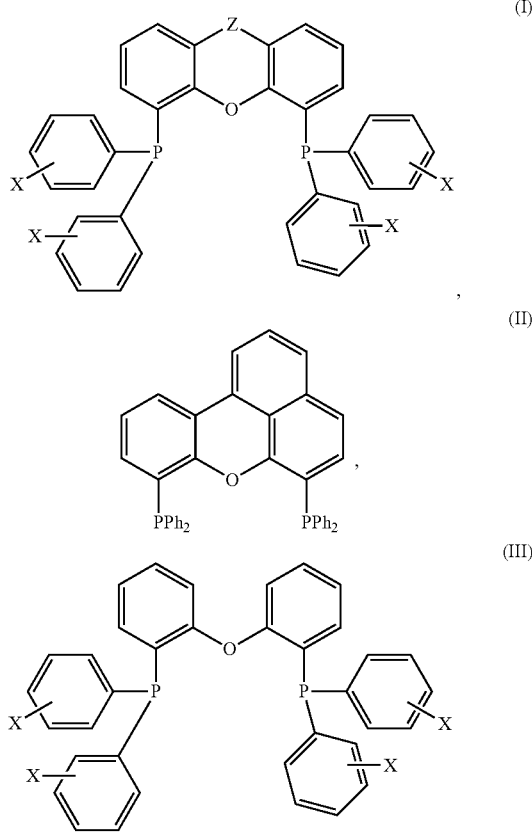

wherein
(i) Z is —O—; —S—; methylene; —C(R)$_2$—; —C(=CR$_2$)—; —P(aryl)-; —P(heteroaryl)-; —Si(R)$_2$—; or —N(R)—;
(ii) each R is independently at each occurrence H, lower alkyl, aryl, or aralkyl; and
(iii) X is independently at each occurrence H, F, Cl, C$_{1-3}$ alkyl, or C$_{1-3}$ alkoxide; the method further comprising adding a sacrificial carboxylic acid anhydride to the reaction mixture during the formation of the olefin product, the sacrificial carboxylic acid anhydride being added in one or more portions each of which is sub-stoichiometric with respect to the precursor carboxylic acid anhydride.

2. The method of claim 1, wherein the precursor carboxylic acid anhydride is formed in situ by the reaction between a precursor carboxylic acid and a stoichiometric amount of the sacrificial carboxylic acid anhydride, the total amount of the sacrificial carboxylic acid anhydride added to the reaction mixture being the sum of the stoichiometric amount and the one or more sub-stoichiometric portions of the sacrificial carboxylic acid anhydride.

3. The method of claim 1, wherein the molar ratio of each portion of the sacrificial carboxylic acid anhydride to the precursor carboxylic acid anhydride is in a range of from about 0.1 to about 0.9.

4. The method of claim 1, wherein the sacrificial carboxylic acid anhydride is converted to its corresponding carboxylic acid during the formation of the olefin product.

5. The method of claim 1, wherein the sacrificial carboxylic acid anhydride comprises acetic anhydride, benzoic anhydride, isobutyric anhydride, propionic anhydride, or pivalic anhydride.

6. The method of claim 1, wherein the organic acid is 3,5,3',5'-tetra-tert-butyl-biphenyl-2,2'-diol.

7. The method of claim 1, wherein the CO and water are removed from the reaction mixture by vacuum distillation.

8. The method of claim 1, wherein the precursor carboxylic acid anhydride is an acid anhydride of at least one fatty acid and the olefin product comprises at least 80 mole % of alpha olefin, relative to the total olefin formed by the method.

9. The method of claim 1, wherein the precursor carboxylic acid anhydride is an acid anhydride of at least one alkyl moiety functionalized by an alkoxycarbonyl, ester, halide, imide, ketone, protected amine, terminal olefin, or substituted aromatic.

10. The method of claim 1, wherein the olefin product comprises at least 80 mole % of alpha olefin, relative to the total olefin formed by the method.

11. The method claim 1, wherein the bidentate bis-phosphine ligand has a bite angle in a range of from about 100 degrees to about 130 degrees.

12. The method of claim 1, wherein the palladium is present in a range of from about 0.01 mole percent to about 0.5 mole percent, relative to the amount of the precursor carboxylic acid anhydride present in the reaction mixture.

13. The method of claim 1, wherein the molar ratio of bidentate bis-phosphine ligand to palladium in the palladium catalyst is in a range of from about 0.9 to about 2.

14. The method claim 1, wherein the bidentate bis-phosphine ligand comprises the structure of Formula (I), in which each X is H.

15. The method of claim 1, wherein the bidentate bis-phosphine ligand comprises the structure of Formula (I) or Formula (II), in which X is independently at each occurrence F, Cl, methyl, or methoxy, and wherein each X is substituted in the 2 or 4 position of the phenyl groups.

16. The method of claim 1, wherein the bidentate bis-phosphine ligand comprises a Xantphos ligand or a DPEphos ligand:

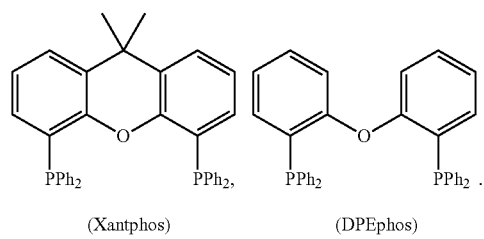

(Xantphos) (DPEphos)

17. The method of claim 1, wherein the palladium catalyst comprising the bidentate bis-phosphine ligand is generated in situ.

18. The method of claim 1, wherein the reaction mixture further comprises an optionally substituted monodentate triarylphosphine or monodentate tri-heteroarylphosphine ligand.

19. The method of claim 18, wherein the reaction mixture further comprises a triphenylphosphine ligand.

20. The method of claim 1, wherein the reaction mixture consists essentially of (a) the precursor carboxylic acid anhydride, (b) the palladium catalyst comprising a bidentate bis-phosphine ligand, (c) the organic acid, and (c) the sub-stoichiometric portions of the sacrificial carboxylic acid anhydride.

21. The method of claim 1, wherein the organic acid is 3,5,3',5'-tetra-tert-butyl-biphenyl-2,2'-diol, benzoic acid, phthalic acid, isophthalic acid, terephthalic acid, benzene-1,3,5-tricarboxylic acid, benzene-1,2,4-tricarboxylic acid, salicylic acid, or salicylamide.

22. The method of claim 1, wherein the organic acid is pentafluorophenol, 2,2'-biphenol; benzene-1,4-diol, (2-hydroxy-phenyl)-phenyl-methanone; 2-hydroxy -isophthalic acid dimethyl ester; 4-hydroxy-isophthalic acid dimethyl ester; 2,6-diphenyl phenol; 2,4,6-triphenyl phenol; or 2,6-di-tert-butyl-4-methyl-phenol.

23. The method of claim 10, wherein the olefin product contains at least 80 mole % and up to 99 mole % of alpha olefin, relative to the total olefin formed by the method.

24. The method of claim 1, operated at a temperature in a range of from about 100° C. to about 160° C., wherein:

(a) the precursor carboxylic acid anhydride is an acid anhydride of at least one fatty acid or is an anhydride of at least one alpha-alkyl moiety functionalized by an alkoxycarbonyl, ester, halide, imide, ketone, protected amine, terminal olefin, or substituted aromatic;

(b) the bidentate bis-phosphine ligand comprises a Xantphos ligand or a DPEphos ligand;

(c) the sacrificial carboxylic acid anhydride comprises acetic anhydride, benzoic anhydride, isobutyric anhydride, propionic anhydride, or pivalic anhydride and is added portionwise in an amount ranging from about 0.1 to about 0.6, relative to the original amount of the precursor carboxylic acid anhydride;

(d) the reaction mixture optionally comprises an optionally substituted monodentate triarylphosphine or optionally substituted monodentate triheteroarylphosphine ligand; wherein the olefin product contains at least 80 mole % and up to 99 mole % of alpha olefin, relative to the total olefin formed by the method.

25. The method of claim 24, wherein the organic acid is 3,5,3',5'-tetra-tert-butyl-biphenyl-2,2'-diol.

* * * * *